US011819503B2

(12) United States Patent
Law et al.

(10) Patent No.: US 11,819,503 B2
(45) Date of Patent: Nov. 21, 2023

(54) METHOD OF TREATING COCCIDIOIDES INFECTION

(71) Applicant: F2G Ltd, Manchester (GB)

(72) Inventors: Derek Law, Manchester (GB); John H. Rex, Manchester (GB); Michael Birch, Manchester (GB); Nathan P. Wiederhold, San Antonio, TX (US); Thomas F. Patterson, San Antonio, TX (US)

(73) Assignees: F2G Ltd, Manchester (GB); Nathan P. Wiederhold, San Antonio, TX (US); Thomas F. Patterson, San Antonio, TX (US)

( * ) Notice: Subject to any disclaimer, the term of this patent is extended or adjusted under 35 U.S.C. 154(b) by 9 days.

(21) Appl. No.: 16/855,346

(22) Filed: Apr. 22, 2020

(65) Prior Publication Data

US 2020/0338072 A1 Oct. 29, 2020

Related U.S. Application Data

(60) Provisional application No. 62/837,623, filed on Apr. 23, 2019.

(51) Int. Cl.
*A61K 31/506* (2006.01)
*A61P 31/10* (2006.01)
*A61K 31/4196* (2006.01)

(52) U.S. Cl.
CPC ........ *A61K 31/506* (2013.01); *A61K 31/4196* (2013.01); *A61P 31/10* (2018.01)

(58) Field of Classification Search
CPC .................................................... A61K 31/506
See application file for complete search history.

(56) References Cited

U.S. PATENT DOCUMENTS

| | | | | |
|---|---|---|---|---|
| 3,202,654 | A | 8/1965 | Gaston | |
| 3,252,970 | A | 5/1966 | Ferdinand | |
| 3,256,279 | A | 6/1966 | George | |
| 3,458,515 | A | 7/1969 | Archibald | |
| 3,573,294 | A | 3/1971 | Long | |
| 3,857,857 | A | 12/1974 | Bella | |
| 4,148,907 | A | 4/1979 | Conti | |
| 4,163,015 | A | 7/1979 | Johnson | |
| 4,316,900 | A | 2/1982 | Wasley | |
| 4,761,424 | A | 8/1988 | Carethers | |
| 4,794,120 | A | 12/1988 | Manoury | |
| 5,750,540 | A | 5/1998 | Tsuchiya | |
| 6,645,976 | B1 | 11/2003 | Dillard | |
| 7,780,988 | B2 | 8/2010 | Beyerinck | |
| 8,524,705 | B2 | 9/2013 | Payne | |
| 8,617,604 | B2 | 12/2013 | Babcock | |
| 8,741,346 | B2 | 6/2014 | Lochard | |
| 8,828,443 | B2 | 9/2014 | Beyerinck | |
| 8,940,800 | B2 | 1/2015 | Babcock | |
| 8,993,574 | B2 | 3/2015 | Sibley | |
| 9,040,033 | B2 | 5/2015 | Miller | |
| 9,452,168 | B2 | 9/2016 | Sibley | |
| 10,201,524 | B2 * | 2/2019 | Sibley | A61P 17/00 |
| 10,596,150 | B2 * | 3/2020 | Sibley | A61P 17/00 |
| 10,973,821 | B2 | 4/2021 | Law et al. | |
| 11,065,228 | B2 * | 7/2021 | Sibley | A61P 11/00 |
| 2005/0032871 | A1 | 2/2005 | Tang | |
| 2005/0090541 | A1 | 4/2005 | Arnaiz | |
| 2006/0058286 | A1 | 3/2006 | Krystal | |
| 2008/0118500 | A1 | 5/2008 | Liu | |
| 2015/0273354 | A1 | 10/2015 | Dobry | |
| 2017/0340607 | A1 | 11/2017 | Sibley | |
| 2019/0314333 | A1 | 10/2019 | Sibley | |

(Continued)

FOREIGN PATENT DOCUMENTS

| | | | |
|---|---|---|---|
| DE | 2253150 | A1 | 5/1973 |
| DE | 2429923 | A1 | 1/1975 |

(Continued)

OTHER PUBLICATIONS

Lara, Drugs Sep. 2017;77(14):1505-1518.*
Wiederhold, Antimicrobial Agents and Chemotherapy, Sep. 2018 vol. 62 Issue 9 e00999-18.*
Wiederhold, Sep. 2018 vol. 62 Issue 9, 1-7.*
Oliver, Proceedings of the National Academy of Sciences of the United States of America (2016), 113(45), 12809-12814.*
Levy, Clinical Infectious Diseases (2013), 56(11), 1573-1578.*
Alvarez, M. et al. (1999). "Synthesis of 1,2-Dihydropyrrolo[1,2-c]Pyrimidin-1-Ones," Journal of Chemical Society pp. 249-255.
Alves, M.J. et al. (2000). "Novel Aziridine Esters by the Addition of Aromatic Nitrogen Heterocycles to a 2H-Azirine-3-Carboxylic Ester," Tetrahedron Letters 41:4991-4995.

(Continued)

*Primary Examiner* — Nizal S Chandrakumar
(74) *Attorney, Agent, or Firm* — MORRISON & FOERSTER LLP

(57) ABSTRACT

The invention relates to the therapeutic use of olorofim, 2-(1,5-dimethyl-3-phenyl-1H-pyrrol-2-yl)-N-(4-(4-(5-fluoropyrimidin-2-yl)piperazin-1-yl)phenyl)-2-oxoacetamide

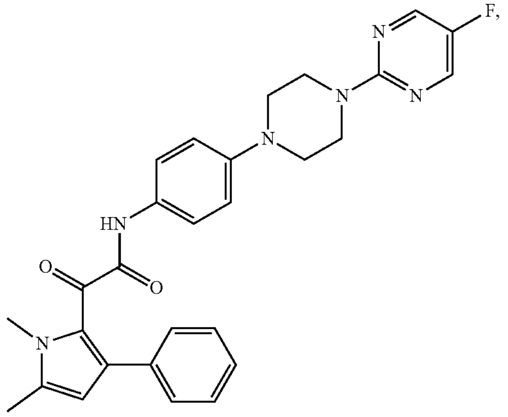

in the prevention and treatment of a fungal infection caused by a *Coccidioides* species.

13 Claims, 9 Drawing Sheets

(56) References Cited

U.S. PATENT DOCUMENTS

| | | | |
|---|---|---|---|
| 2019/0328737 | A1 | 10/2019 | Law |
| 2020/0179340 | A1 | 6/2020 | Sibley |
| 2021/0186967 | A1 | 6/2021 | Law et al. |

FOREIGN PATENT DOCUMENTS

| | | | |
|---|---|---|---|
| DE | 2751571 | A1 | 5/1978 |
| EA | 200101172 | A1 | 4/2002 |
| EP | 0252809 | A2 | 1/1988 |
| EP | 0505321 | A2 | 9/1992 |
| EP | 0747756 | A1 | 12/1996 |
| EP | 0901786 | A2 | 3/1999 |
| EP | 1239835 | A1 | 9/2002 |
| EP | 1543841 | A1 | 6/2005 |
| EP | 1857113 | A2 | 11/2007 |
| EP | 1027887 | B1 | 8/2008 |
| EP | 1886673 | B1 | 10/2011 |
| EP | 1653928 | B1 | 3/2012 |
| EP | 2529731 | A1 | 12/2012 |
| EP | 2626361 | A1 | 8/2013 |
| EP | 2636409 | A1 | 9/2013 |
| FR | 1381256 | A | 12/1964 |
| FR | 1556822 | A | 2/1969 |
| GB | 1051723 | A | 12/1966 |
| GB | 1208014 | A | 10/1970 |
| GB | 1476503 | A | 6/1977 |
| JP | 57142966 | A | 9/1982 |
| JP | 57144255 | A | 9/1982 |
| JP | 62081369 | A | 4/1987 |
| JP | 09249669 | A | 9/1997 |
| RU | 2152392 | C1 | 7/2000 |
| WO | 199601822 | A1 | 1/1996 |
| WO | 199603383 | A1 | 2/1996 |
| WO | 199633973 | A1 | 10/1996 |
| WO | 199856422 | A1 | 12/1998 |
| WO | 199962881 | A2 | 12/1999 |
| WO | 200032588 | A2 | 6/2000 |
| WO | 200066580 | A2 | 11/2000 |
| WO | 200032588 | A3 | 2/2001 |
| WO | 200108572 | A1 | 2/2001 |
| WO | 200066580 | A3 | 4/2001 |
| WO | 200147495 | A1 | 7/2001 |
| WO | 200185723 | A1 | 11/2001 |
| WO | 2002085301 | A2 | 10/2002 |
| WO | 2002085907 | A1 | 10/2002 |
| WO | 2002098876 | A1 | 12/2002 |
| WO | 2003000680 | A1 | 1/2003 |
| WO | 2002085301 | A3 | 2/2003 |
| WO | 2003064397 | A1 | 8/2003 |
| WO | 2003072028 | A2 | 9/2003 |
| WO | 2003072028 | A3 | 12/2003 |
| WO | 2004082606 | A2 | 9/2004 |
| WO | 2004082606 | A3 | 1/2005 |
| WO | 2006105289 | A1 | 10/2006 |
| WO | 2006113875 | A2 | 10/2006 |
| WO | 2006123145 | A1 | 11/2006 |
| WO | 2007009083 | A2 | 1/2007 |
| WO | 2007015866 | A2 | 2/2007 |
| WO | 2006113875 | A3 | 5/2007 |
| WO | 2007009083 | A3 | 7/2007 |
| WO | 2007015866 | A3 | 8/2007 |
| WO | 2007092681 | A2 | 8/2007 |
| WO | 2007109605 | A2 | 9/2007 |
| WO | 2007109605 | A3 | 1/2008 |
| WO | 2008046082 | A2 | 4/2008 |
| WO | 2008062182 | A1 | 5/2008 |
| WO | 2008046082 | A3 | 6/2008 |
| WO | 2008092057 | A2 | 7/2008 |
| WO | 2008092057 | A3 | 9/2008 |
| WO | 2008106860 | A1 | 9/2008 |
| WO | 2008145963 | A1 | 12/2008 |
| WO | 2009010842 | A2 | 1/2009 |
| WO | 2007092681 | A3 | 3/2009 |
| WO | 2009010842 | A3 | 3/2009 |
| WO | 2009129301 | A2 | 10/2009 |
| WO | 2009130481 | A1 | 10/2009 |
| WO | 2009129301 | A3 | 12/2009 |
| WO | 2009144473 | A1 | 12/2009 |
| WO | 2010045281 | A2 | 4/2010 |
| WO | 2010045281 | A3 | 8/2010 |
| WO | 2010126967 | A1 | 11/2010 |
| WO | 2012060448 | A1 | 5/2012 |
| WO | 2013078500 | A1 | 6/2013 |
| WO | 2013154607 | A1 | 10/2013 |
| WO | 2014031418 | A1 | 2/2014 |
| WO | 2014031422 | A1 | 2/2014 |
| WO | 2014114575 | A1 | 7/2014 |
| WO | 2015007759 | A1 | 1/2015 |
| WO | 2015007760 | A1 | 1/2015 |
| WO | 2015082562 | A1 | 6/2015 |
| WO | 2015150763 | A1 | 10/2015 |
| WO | 2016079536 | A1 | 5/2016 |
| WO | 2017203270 | A1 | 11/2017 |

OTHER PUBLICATIONS

Ames, D.E. et al. (1959, e-pub. Jan. 1, 1959). "The Preparation of Aminoalkylpyrrocolines," Journal of Chemical Society 124:620-622.

Anonymous (Sep. 17, 2017). "In Vivo Efficacy of Orally Dosed F901318, in a Murine Model of Disseminated Aspergillosis", 55th Intersci Conf Antimicrob Agents Chemother (ICAAC), retrieved from the Internet: URL:https://integrity.thomson-pharma.com/integrity/xmixs1/pk_ref_listxml_show_ficha_ref?p_ref_id=2393484, last visited Nov. 7, 2017, 1 page.

Anonymous (Sep. 4, 2014). "F2G Begins F901318 Phase I Clinical Study for Treatment of Aspergillus Infections", News Medical Life Sciences, Sep. 4, 2014, retrieved from URL:http://www.news-medical.net/news/20140904/F2G-begins-F901318-Phase-I-clinical-study-for-treatment-of-aspergillus-infections.aspx, 2 pages.

Anonymous. (2012). "Diethyl Ether," retrieved from http:www.merckmillipore.com/chemicals/diethyl-ether/MDA_CHEM-100926/p_NgGb.s1Lay4AAAEW8uEfVhTI, last visited on Jul. 11, 2012, 4 pages.

Anonymous. (Mar. 2006-Nov. 2013). "Anacor Pharmaceuticals Scientific Presentations", 7 pages.

Archibald, J.L. et al. (1974). "Benzamidopiperidines. 2. Heterocyclic Compounds Related to Indoramin," Journal of Medicinal Chemistry 17(7):736-739.

Archibald, J.L. et al. (Sep. 1967). "New Reactions of Pyrroles. II. Preparation and Reactions of Pyrroleglyoxyloyl Derivatives," Journal of Heterocyclic Chemistry 4:335-338.

Battersby, A.R. et al. (1992, e-pub. Jan. 1, 1992). "Synthetic Studies Relevant to Biosynthetic Research on Vitamin B12. Part 10. Construction of the East and West Building Blocks for Synthesis of Isobacteriochlorins," Journal of Chemical Society 17:2175-2187.

Bentov, M. et al. (1964). "4-Fluoroindole and Derivatives," Israel Journal of Chemistry 2:25-28.

Birchall, G.R. et al. (1971). "The Chlorination of Pyrroles. Part II," Canadian Journal of Chemistry 49:919-922.

Black, D.S.C. et al. (1996). "Reaction of Some 4,6-Dimethoxyindoles with Oxalyl Chloride," Tetrahedron 52(26):8925-8936.

Black, D.S.C. et al. (1996). "The Indol-2-Ylglyoxylamide Moiety: A New Building Block for the Design and Self-Assembly of Hydrogen Bond Networks," Journal of American Chemical Society 118(34):8148-8149.

Black, D.S.C. et al. (2000). "Formation of C-Amido-Calix[3]Indoles from 2'- and 7'-Indolylglyoxylamides," Tetrahedron 56:8513-8524.

Bohusch, M. et al. (1991). "Consequences of a Diminution of the Porphyrin π-System: Attempted Syntheses of Bacteriophin and Chlorophin," Liebigs Annalen der Chemie pp. 67-70. (English Abstract Only).

Borthwick, A.D. et al. (Jan. 3, 2002, e-pub. Dec. 5, 2001). "Design and synthesis of Pyrrolidine-5,5-trans-Lactams (5-Oxohexahdropyrrolo[3,2-b]Pyrroles) as Novel Mechanism-Based Inhibitors of Human Cytomegalovirus Protease. 2. Potency and Chirality," Journal of Medicinal Chemistry 45(1):1-18.

(56) References Cited

OTHER PUBLICATIONS

Buil, J.B. et al. (2017, e-pub. Jun. 10, 2017). "In vitro Activity of the Novel Antifungal Compound F901318 Against Difficuit-to-Treat Aspregiilus Isolates," J Antimicrob. Chermother. 72, 2548-2552.
Cameron, B.D. et al. (1973). "The Synthesis and Metabolic Fate of 14C-Viminol, a New Analgesic, in the Rat and the Dog," Arzneimittel-Forshung/Drug Res. 23(5):708-712.
Cardellini, M. et al. (Feb. 1977). "Indolizine Derivatives with Biological Activity I: N'-Substituted Hydrazides of Indolizine-2-Carboxylic Acid," Journal of Pharmaceutical Sciences 66(2):259-262.
CAS Registry No. 1002010-45-8, created Feb. 7, 2008, last accessed Oct. 30, 2013, 1 page.
CAS Registry No. 1002010-93-6, created Feb. 7, 2008, last accessed Oct. 30, 2013, 2 pages.
CAS Registry No. 1004172-59-1, created Feb. 18, 2008, last accessed Oct. 30, 2013, 1 page.
CAS Registry No. 1004425-72-2, created Feb. 19, 2008, last accessed Oct. 30, 2013, 1 page.
CAS Registry No. 1026853-99-5 created Jun. 9, 2008, last accessed Feb. 2, 2012, 1 page.
CAS Registry No. 1027826-94-3, created Jun. 9, 2008, last accessed Feb. 2, 2012, 1 page.
CAS Registry No. 1029775-76-5, created Jun. 22, 2008, last accessed Feb. 2, 2012, 2 pages.
CAS Registry No. 1056748-82-3, created Oct. 3, 2008, last accessed Feb. 2, 2012, 1 page.
CAS Registry No. 130761-64-7, created Nov. 30, 1990, last accessed Feb. 2, 2012, 1 page.
CAS Registry No. 130761-68-1, created Nov. 30, 1990, last accessed Feb. 2, 2012, 2 pages.
CAS Registry No. 145045-69-8, created Dec. 25, 1992, last accessed Feb. 2, 2012, 2 pages.
CAS Registry No. 15940-17-7, created Nov. 16, 1984, last accessed Feb. 2, 2012, 1 page.
CAS Registry No. 15940-18-8, created Nov. 16, 1984, last accessed Feb. 2, 2012, 1 page.
CAS Registry No. 15940-19-9, created Nov. 16, 1984, last accessed Feb. 2, 2012, 1 page.
CAS Registry No. 15940-20-2, created Nov. 16, 1984, last accessed Feb. 2, 2012, 2 pages.
CAS Registry No. 15940-21-3, created Nov. 16, 1984 last accessed Feb. 2, 2012, 1 page.
CAS Registry No. 15940-22-4, created Nov. 16, 1984, last accessed Feb. 2, 2012, 2 pages.
CAS Registry No. 15940-23-5, created Nov. 16, 1984, last accessed Feb. 2, 2012, 1 page.
CAS Registry No. 15940-24-6, created Nov. 16, 1984, last accessed Feb. 2, 2012, 2 pages.
CAS Registry No. 15940-25-7, created Nov. 16, 1984, last accessed Feb. 2, 2012, 1 page.
CAS Registry No. 171845-45-8, created Dec. 29, 1995, last accessed Feb. 2, 2012, 2 pages.
CAS Registry No. 171854-40-3, created Dec. 29, 1995, last accessed Feb. 2, 2012, 1 page.
CAS Registry No. 171854-41-4, created Dec. 29, 1995, last accessed Feb. 2, 2012, 2 pages.
CAS Registry No. 171854-42-5, created Dec. 29, 1995, last accessed Feb. 2, 2012, 2 pages.
CAS Registry No. 171854-43-6, created Dec. 29, 1995, last accessed Feb. 2, 2012, 2 pages.
CAS Registry No. 171854-44-7, created Dec. 29, 1995, last accessed Feb. 2, 2012, 1 page.
CAS Registry No. 171854-46-9, created Dec. 29, 1995, last accessed Feb. 2, 2012, 1 page.
CAS Registry No. 171854-47-0, created Dec. 29, 1995, last accessed Feb. 2, 2012, 2 pages.
CAS Registry No. 185030-21-1, created Jan. 15, 1997, last accessed Feb. 2, 2012, 1 page.
CAS Registry No. 208765-70-2, created Jul. 22, 1998, last accessed Feb. 2, 2012, 1 page.
CAS Registry No. 208765-71-3, created Jul. 22, 1998, last accessed Feb. 2, 2012, 1 page.
CAS Registry No. 208765-72-4, created Jul. 22, 1998, last accessed Feb. 2, 2012, 2 pages.
CAS Registry No. 208765-73-5, created Jul. 22, 1998, last accessed Feb. 2, 2012, 1 page.
CAS Registry No. 208765-74-6, created Jul. 22, 1998, last accessed Feb. 2, 2012, 1 page.
CAS Registry No. 208765-75-7, created Jul. 22, 1998, last accessed Feb. 2, 2012, 1.
CAS Registry No. 208765-76-8, created Jul. 22, 1998, last accessed Feb. 2, 2012, 1 page.
CAS Registry No. 208765-77-9, created Jul. 22, 1998, last accessed Feb. 2, 2012, 2 pages.
CAS Registry No. 208765-78-0, created Jul. 22, 1998, last accessed Feb. 2, 2012, 1 page.
CAS Registry No. 208765-79-1, created Jul. 22, 1998, last accessed Feb. 2, 2012, 2 pages.
CAS Registry No. 208765-80-4, created Jul. 22, 1998, last accessed Feb. 2, 2012, 1 page.
CAS Registry No. 208765-81-5, created Jul. 22, 1998, last accessed Feb. 2, 2012, 2 pages.
CAS Registry No. 208765-82-6, created Jul. 22, 1998, last accessed Feb. 2, 2012, 1 page.
CAS Registry No. 208765-83-7, created Jul. 22, 1998, last accessed Feb. 2, 2012, 2 pages.
CAS Registry No. 208765-84-8, created Jul. 22, 1998, last accessed Feb. 2, 2012, 1 page.
CAS Registry No. 208765-85-9, created Jul. 22, 1998, last accessed Feb. 2, 2012, 2 pages.
CAS Registry No. 208765-86-0, created Jul. 22, 1998, last accessed Feb. 2, 2012, 1 page.
CAS Registry No. 208765-87-1, created Jul. 22, 1998, last accessed Feb. 2, 2012, 2 pages.
CAS Registry No. 208765-88-2, created Jul. 22, 1998, last accessed Feb. 2, 2012, 1 page.
CAS Registry No. 208765-89-3, created Jul. 22, 1998, last accessed Feb. 2, 2012, 2 pages.
CAS Registry No. 208765-90-6, created Jul. 22, 1998, last accessed Feb. 2, 2012, 1 page.
CAS Registry No. 208765-91-7, created Jul. 22, 1998, last accessed Feb. 2, 2012, 1 page.
CAS Registry No. 208765-92-8, created Jul. 22, 1998, last accessed Feb. 2, 2012, 1 page.
CAS Registry No. 208765-93-9, created Jul. 22, 1998, last accessed Feb. 2, 2012, 1 page.
CAS Registry No. 208765-94-0, created Jul. 22, 1998, last accessed Feb. 2, 2012, 2 pages.
CAS Registry No. 208765-95-1, created Jul. 22, 1998, last accessed Feb. 2, 2012, 1 page.
CAS Registry No. 208765-96-2, created Jul. 22, 1998, last accessed Feb. 2, 2012, 2 pages.
CAS Registry No. 208766-03-4, created Jul. 22, 1998, last accessed Feb. 2, 2012, 1 page.
CAS Registry No. 208766-04-5, created Jul. 22, 1998, last accessed Feb. 2, 2012, 2 pages.
CAS Registry No. 208766-05-6, created Jul. 22, 1998, last accessed Feb. 2, 2012, 1 page.
CAS Registry No. 23502-48-9, created Nov. 16, 1984, last accessed Feb. 2, 2012, 2 pages.
CAS Registry No. 263554-36-5, created May 2, 2000, last accessed Feb. 2, 2012, 1 page.
CAS Registry No. 263554-39-8, created May 2, 2000, last accessed Feb. 2, 2012, 2 pages.
CAS Registry No. 26883-51-2, created Nov. 16, 1984, last accessed Feb. 2, 2012, 1 page.
CAS Registry No. 292063-96-8, created Oct. 2, 2000, last accessed Feb. 2, 2012, 1 page.
CAS Registry No. 292064-15-4, created Oct. 2, 2000, last accessed Feb. 2, 2012, 2 pages.

(56) References Cited

OTHER PUBLICATIONS

CAS Registry No. 31709-75-8, created Nov. 16, 1984, last accessed Feb. 2, 2012, 2 pages.
CAS Registry No. 31709-76-9, created Nov. 16, 1984, last accessed Feb. 2, 2012, 1 page.
CAS Registry No. 31709-77-0, created Nov. 16, 1984, last accessed Feb. 2, 2012, 1 page.
CAS Registry No. 31710-23-3, created Nov. 16, 1984, last accessed Feb. 2, 2012, 1 page.
CAS Registry No. 364044-26-8, created Oct. 23, 2001, last accessed Feb. 2, 2012, 1 page.
CAS Registry No. 364044-30-4, created Oct. 23, 2001, last accessed Feb. 2, 2012, 2 pages.
CAS Registry No. 36793-47-2, created Nov. 16, 1984, last accessed Feb. 2, 2012, 2 pages.
CAS Registry No. 3758-62-1, created Nov. 16, 1984, last accessed Feb. 2, 2012, 1 page.
CAS Registry No. 3768-71-6, created Nov. 16, 1984, last accessed Feb. 2, 2012, 1 page.
CAS Registry No. 3768-72-7, created Nov. 16, 1984, last accessed Feb. 2, 2012, 1 page.
CAS Registry No. 3768-82-9, created Nov. 16, 1984, last accessed Feb. 2, 2012, 2 pages.
CAS Registry No. 396733-55-4, created Feb. 28, 2002, last accessed Feb. 2, 2012, 1 page.
CAS Registry No. 41596-37-6, created Nov. 16, 1984, last accessed Feb. 2, 2012, 1 page.
CAS Registry No. 42060-03-7, created Nov. 16, 1984, last accessed Feb. 2, 2012, 2 pages.
CAS Registry No. 42060-05-9, created Nov. 16, 1984, last accessed Feb. 2, 2012, 1 page.
CAS Registry No. 42221-74-9, created Nov. 16, 1984, last accessed Feb. 2, 2012, 2 pages.
CAS Registry No. 422507-64-0, created May 29, 2002, last accessed Feb. 2, 2012, 1 page.
CAS Registry No. 422507-66-2, created May 29, 2002, last accessed Feb. 2, 2012, 1 page.
CAS Registry No. 422507-69-5, created May 29, 2002, last accessed Feb. 2, 2012, 1 page.
CAS Registry No. 43084-49-7, created Nov. 16, 1984, last accessed Feb. 2, 2012, 1 page.
CAS Registry No. 4380-46-5, created Nov. 16, 1984, last accessed Feb. 2, 2012, 1 page.
CAS Registry No. 4595-83-9, created Nov. 16, 1984, last accessed Feb. 2, 2012, 2 pages.
CAS Registry No. 477709-20-9, created Dec. 27, 2002, last accessed Feb. 2, 2012, 2 pages.
CAS Registry No. 477709-21-0, created Dec. 27, 2002 last accessed Feb. 2, 2012, 2 pages.
CAS Registry No. 477709-22-1, created Dec. 27, 2002, last accessed Feb. 2, 2012, 1 page.
CAS Registry No. 477709-24-3, created Dec. 27, 2002, last accessed Feb. 2, 2012, 2 pages.
CAS Registry No. 477709-25-4, created Dec. 27, 2002, last accessed Feb. 2, 2012, 1 page.
CAS Registry No. 477709-26-5, created Dec. 27, 2002, last accessed Feb. 2, 2012, 2 pages.
CAS Registry No. 477709-27-6, created Dec. 27, 2002, last accessed Feb. 2, 2012, 1 page.
CAS Registry No. 477709-28-7, created Dec. 27, 2002, last accessed Feb. 2, 2012, 2 pages.
CAS Registry No. 477709-29-8, created Dec. 27, 2002, last accessed Feb. 2, 2012, 1 page.
CAS Registry No. 477709-30-1 created Dec. 27, 2002, last accessed Feb. 2, 2012, 2 pages.
CAS Registry No. 477857-72-0, created Dec. 31, 2002, last accessed Feb. 2, 2012, 1 page.
CAS Registry No. 477857-73-1, created Dec. 31, 2002, last accessed Feb. 2, 2012, 2 pages.
CAS Registry No. 477857-74-2, created Dec. 31, 2002, last accessed Feb. 2, 2012, 1 page.
CAS Registry No. 477857-75-3, created Dec. 31, 2002, last accessed Feb. 2, 2012, 2 pages.
CAS Registry No. 477857-76-4, created Dec. 31, 2002, last accessed Feb. 2, 2012, 1 page.
CAS Registry No. 477857-77-5, created Dec. 31, 2002, last accessed Feb. 2, 2012, 2 pages.
CAS Registry No. 477857-78-6, created Dec. 31, 2002, last accessed Feb. 2, 2012, 1 page.
CAS Registry No. 477857-79-7, created Dec. 31, 2002, last accessed Feb. 2, 2012, 2 pages.
CAS Registry No. 477857-80-0, created Dec. 31, 2002, last accessed Feb. 2, 2012, 1 page.
CAS Registry No. 477857-81-1, created Dec. 31, 2002, last accessed Feb. 2, 2012, 2 pages.
CAS Registry No. 477863-31-3, created Dec. 31, 2002, last accessed Feb. 2, 2012, 1 page.
CAS Registry No. 4/7863-34-6, created Dec. 31, 2002, last accessed Feb. 2, 2012, 2 pages.
CAS Registry No. 477863-37-9, created Dec. 31, 2002, last accessed Feb. 2, 2012, 1 page.
CAS Registry No. 477871-94-6, created Dec. 31, 2002, last accessed Feb. 2, 2012, 2 pages.
CAS Registry No. 477871-95-7, created Dec. 31, 2002, last accessed Feb. 2, 2012, 1 page.
CAS Registry No. 477871-96-8, created Dec. 31, 2002, last accessed Feb. 2, 2012, 1 page.
CAS Registry No. 477871-97-9, created Dec. 31, 2002, last accessed Feb. 2, 2012, 1 page.
CAS Registry No. 477871-98-0, created Dec. 31, 2002, last accessed Feb. 2, 2012, 1 page.
CAS Registry No. 477871-99-1 created Dec. 31, 2002, last accessed Feb. 2, 2012, 2 pages.
CAS Registry No. 477872-00-7, created Dec. 31, 2002, last accessed Feb. 2, 2012, 1 page.
CAS Registry No. 477872-01-8, created Dec. 31, 2002, last accessed Feb. 2, 2012, 2 pages.
CAS Registry No. 477872-02-9, created Dec. 31, 2002, last accessed Feb. 2, 2012, 1 page.
CAS Registry No. 477872-03-0, created Dec. 31, 2002, last accessed Feb. 2, 2012, 1 page.
CAS Registry No. 477872-04-1, created Dec. 31, 2002, last accessed Feb. 2, 2012, 2 pages.
CAS Registry No. 477872-05-2, created Dec. 31, 2002, last accessed Feb. 2, 2012, 1 page.
CAS Registry No. 477872-69-8, created Dec. 31, 2002, last accessed Feb. 2, 2012, 2 pages.
CAS Registry No. 477872-70-1, created Dec. 31, 2002, last accessed Feb. 2, 2012, 1 page.
CAS Registry No. 477872-71-2, created Dec. 31, 2002, last accessed Feb. 2, 2012, 2 pages.
CAS Registry No. 477872-72-3, created Dec. 31, 2002, last accessed Feb. 2, 2012, 1 page.
CAS Registry No. 477872-73-4 created Dec. 31, 2002, last accessed Feb. 2, 2012, 2 pages.
CAS Registry No. 477872-74-5, created Dec. 31, 2002, last accessed Feb. 2, 2012, 1 page.
CAS Registry No. 477872-75-6, created Dec. 31, 2002, last accessed Feb. 2, 2012, 2 pages.
CAS Registry No. 477872-76-7, created Dec. 31, 2002, last accessed Feb. 2, 2012, 1 page.
CAS Registry No. 477872-77-8, created Dec. 31, 2002, last accessed Feb. 2, 2012, 1 page.
CAS Registry No. 477872-78-9, created Dec. 31, 2002, last accessed Feb. 2, 2012, 2 pages.
CAS Registry No. 477872-79-0, created Dec. 31, 2002, last accessed Feb. 2, 2012, 1 page.
CAS Registry No. 477872-80-3, created Dec. 31, 2002, last accessed Feb. 2, 2012, 2 pages.
CAS Registry No. 485843-91-2, created Feb. 5, 2003, last accessed Feb. 2, 2012, 1 page.

(56) References Cited

OTHER PUBLICATIONS

CAS Registry No. 485843-92-3, created Feb. 5, 2003, last accessed Feb. 2, 2012, 1 page.
CAS Registry No. 53391-28-9, created Nov. 16, 1984, last accessed Feb. 2, 2012, 2 pages.
CAS Registry No. 53391-29-0, created Nov. 16, 1984, last accessed Feb. 2, 2012, 1 page.
CAS Registry No. 53391-30-3, created Nov. 16, 1984, last accessed Feb. 2, 2012, 2 pages.
CAS Registry No. 53391-52-9, created Nov. 16, 1984, last accessed Feb. 2, 2012, 1 page.
CAS Registry No. 53391-63-2, created Nov. 16, 1984, last accessed Feb. 2, 2012, 2 pages.
CAS Registry No. 65473-58-7, created Nov. 16, 1984, last accessed Feb. 2, 2012, 1 page.
CAS Registry No. 655223-84-0, created Feb. 27, 2004, last accessed Feb. 2, 2012, 1 page.
CAS Registry No. 655223-85-1, created Feb. 27, 2004 last accessed Feb. 2, 2012, 2 pages.
CAS Registry No. 6616-51-9, created Nov. 16, 1984, last accessed Feb. 2, 2012, 1 page.
CAS Registry No. 68803-72-5, created Nov. 16, 1984, last accessed Feb. 2, 2012, 2 pages.
CAS Registry No. 773098-60-5, created Nov. 1, 2004, last accessed Feb. 2, 2012, 1 page.
CAS Registry No. 773098-61-6, created Nov. 1, 2004, last accessed Feb. 2, 2012, 2 pages.
CAS Registry No. 802313-56-0, created Dec. 25, 2004, last accessed Feb. 2, 2012, 1 page.
CAS Registry No. 81729-69-3, created Nov. 16, 1984, last accessed Feb. 2, 2012, 1 page.
CAS Registry No. 81741-58-4, created Nov. 16, 1984, last accessed Feb. 2, 2012, 1 page.
CAS Registry No. 83996-64-9, created Nov. 16, 1984, last accessed Feb. 2, 2012, 1 page.
CAS Registry No. 860610-36-2, created Aug. 17, 2005, last accessed Feb. 2, 2012, 1 page.
CAS Registry No. 860610-37-3, created Aug. 17, 2005, last accessed Feb. 2, 2012, 1 page.
CAS Registry No. 860649-79-2, created Aug. 17, 2005, last accessed Feb. 2, 2012, 1 page.
CAS Registry No. 860649-80-5, created Aug. 17, 2005, last accessed Feb. 2, 2012, 1 page.
CAS Registry No. 866010-45-9, created Oct. 25, 2005, last accessed Feb. 2, 2012, 1 page.
CAS Registry No. 866010-46-0, created Oct. 25, 2005, last accessed Feb. 2, 2012, 2 pages.
CAS Registry No. 866010-47-1, created Oct. 25, 2005, last accessed Feb. 2, 2012, 1 page.
CAS Registry No. 866010-76-6, created Oct. 25, 2005, last accessed Feb. 2, 2012, 2 pages.
CAS Registry No. 866010-82-4, created Oct. 25, 2005, last accessed Feb. 2, 2012, 1 page.
CAS Registry No. 866010-83-5, created Oct. 25, 2005, last accessed Feb. 2, 2012, 2 pages.
CAS Registry No. 866010-85-7, created Oct. 25, 2005, last accessed Feb. 2, 2012, 1 page.
CAS Registry No. 866042-95-7, created Oct. 25, 2005, last accessed Feb. 2, 2012, 1 page.
CAS Registry No. 866042-98-0, created Oct. 25, 2005, last accessed Feb. 2, 2012, 1 page.
CAS Registry No. 866042-99-1, created Oct. 25, 2005, last accessed Feb. 2, 2012, 1 page.
CAS Registry No. 866043-03-0, created Oct. 25, 2005, last accessed Feb. 2, 2012, 2 pages.
CAS Registry No. 866043-06-3, created Oct. 25, 2005, last accessed Feb. 2, 2012, 1 page.
CAS Registry No. 945220-52-0, created Aug. 21, 2007, last accessed Feb. 2, 2012, 1 page.
CDC. (Nov. 16, 2015). "Aspergillosis Risk and Prevention," retrieved from http://www.cdc.fungal/diseases/aspergillosis/risk-prevention.html, last visited Nov. 16, 2015, 3 pages.
CDC. (Nov. 16, 2015). "Fungal Diseases," retrieved from http://www.cdc.fungal/diseases/aspergillosis/risk-prevention.html, last visited Nov. 16, 2015, 2 pages.
Chemcats. (Feb. 13, 2008). "1H-Pyrrole-2-Acetamide, N-(4-Bromophenyl)-1-(2-Chloro-4-Nitrophenyl)-α-Oxo-," Ambinter Stock Screening Collection, 5 pages.
Chemcats. (Feb. 18, 2008). "1H-Pyrrole-2-Acetamide, N- (2,4-Dichlorophenyl)-1-Methyl-α-Oxo-," Interchim Intermediates 5 pages.
Chemcats. (Jan. 25, 2008). "Benzo [b] Thiophene-2-Carboxylic Acid, 3-[2- [[(4-Methoxyphenyl) Amino] Oxoacetyl]-1H-Pyrrol-1-y1]-, Methyl Ester," Ryan Scientific Screening Library 5 pages.
Chiarino, D. et al. (1978). "Stereochemistry of Viminol, a Novel Central Analgesic," Arzneimittel-Forshung/Drug Res. 28(11):1554-1561.
Cook, A.H. et al. (1949, e-pub. Jan. 1, 1949). "Studies in the Azole Series. Part XXIV. The Interaction of Carbonyl Compounds and 2-Thio-5-Thiazolidone," Journal of Chemical Society 633:3007-3012.
Crowley, K.J. et al. (1957). "Intermediates for the Synthesis of Optically Active Methyl-Substituted Long-Chain Acids. Part II," Journal of the Chemical Society 2931-2934.
Dannhardt, G. et al. (1979). "Synthese und Eigenschaften von 2,3-Dihydro-1H-Pyrrolizinen,"Arch. Pharm. 312:896-907. (English Abstract).
Dannhardt, G. et al. (1994). "Nonsteroidal Antiinflammatory Agents, XVIII: C-5 Functionalized 6,7-Diphenyl-2,3-Dihydro-1H-Pyrrolizines as Inhibitors of Bovine Cyclooxygenase and 5-Lipoxygenase," Arch Pharm 327:509-514.
Dannhardt, V.G. et al. (1986). "Antiphlogistische 2,3-Dihydro-1H-Pyrrolizine, 11. Mitt. Dihydropyrrolizinyl-Substituierte 2-Aminoethanol- und Glykosäure-Derivate," Chemiker-Zeitung 110(3):124-127. (English Abstract).
Dorby et al. (2009). "A Model-Based Methodology for Spray-Drying Process Development," J. Pharm, Innov. 4:133-142.
Dumoulin, H. et al. (1998). "2-Oxo-2-(Pehn-2-Ylpyrrol-2-Yl)Acetamides as Potential Anxiolytic Agents: Synthesis and Affinity at the Central Benzodiazepine Receptor," European Journal of Medicinal Chemistry 33:201-207.
Dyke, S.F. et al. (1978). "Pavinane and Isopavinane Alkaloids," Tetrahedron 34:241-245.
Ertl, P. et al. (2000). "Fast Calculation of Molecular Polar Surface Area as a Sum of Fragment-Based Contributions and Its Application to the Prediction of Drug Transport Properties," J. Med. Chem. 43(20):3714-3717.
Fryer, R.I. et al. (Dec. 1967). "Quinazolines and 1,4-Benzodiazepines. XXXVII. Synthesis and Rearrangements of a Substituted 5-Phenyl-1H-1,4-Benzodiazepine," Journal of Organic Chemistry 32:3798-3803.
Galbraith, A. et al. (Jan. 20, 1961). "The Formation of Cycl[3,2,2]azine Derivatives via the Reaction of Pyrrocoline with Dimethyl Acetylenedicarboxylate," Journal of the American Chemical Society 83:453-458.
Groll, A.H. et al. (1996). "Trends in the Postmortem Epidemiology of Invasive Fungal Infections at a University Hospital," Journal of Infection 33:23-32.
Hagishita, S. et al. (1996). "Potent Inhibitors of Secretory Phospholipase A2: Synthesis and Inhibitory Activities of Indolizine and Indene Derivatives," Journal of Medicinal Chemistry 39(19):3636-3658.
Harald (Sep. 29, 2015). "Two New Antifungals Presented at ICAAC San Diego," retrieved from http://allphasepharma.com/dir/2015/09/29/1969/two-new-antifungals-presented-at-icaac-sa . . . , lasted visited Jun. 18, 2020, 3 pages.
Hope, W.W. et al. (Aug. 22, 2017), "Pharmacodynamics of the Orotomides against Aspergillus fumigatus: New Opportunities for Treatment of Multidrug-Resistant Fungal Disease," mBio 8(4):e01157-17, 17 pages.
Hudack, R.A. et al. (2006, e-pub. Jan. 14, 2006). "Design, Synthesis, and Biological Activity of Novel Polycyclic Aza-Amide FKBP12 Ligands," Journal of Medicinal Chemistry 49(3):1202-1206.

(56) References Cited

OTHER PUBLICATIONS

Ignatovich, J. et al. (2008). "Synthesis of Functionalized Benzyl Amines by the Reductive Alkylation of Heterocyclic and Heteroaromatic Amines with Arylaldehydes and preparation of the Intermediates for New Synthetic Biomolecules," ARKAT-USA, Inc. (ix):42-51.
Islam, I. et al. (2007, e-pub. Apr. 27, 2007). "Indolinone Based Phosphoinositide-Dependent Kinase-1 (PDK1) Inhibitors. Part 1: Design, Synthesis and Biological Activity," Bioorganic & Medicinal Chemistry Letters 17:3814-3818.
Keawin, T. et al. (2005, e-pub. Dec. 10, 2004). "Reaction of Some 4,6-Dimethoxyindoles with Nitric Acid: Nitration and Oxidative Dimerisation," Tetrahedron 61:853-861.
Leo, A. et al. (Dec. 1971). "Partition Coefficients and Their Uses," Chemical Reviews 71(6):525-616.
Mahiout, Z. et al. (2008, e-pub. Feb. 28, 2008). "Solvent-Dependent Oxidations of 5- and 6-Azaindoles to Trioxopyrrolopyridines and Functionalised Azaindoles," Organic & Biomolecular Chemistry 6:1364-1376.
Mao, W. et al. (Date Unknown) "AN2718 Has Broad Spectrum Antifungal Activity Necessary for the Topical Treatment of Skin and Nail Fungal Infections," P2422, 7 pages.
McDonell et al. (Jan. 1999). "Antiseptics and Disinfectants: Activity, Action, and Resistance," Clinical Microbiology Reviews 12(1):147-179.
Nourmohammadian, F. et al. (2005, e-pub. Jan. 21, 2005). "An AB Initio Molecular Orbital Study of Structural Isomers of Diketopyrrolopyrrole," Dyes and Pigments 67:15-20.
Nowaczyk, A. et al. (2008). "Triazole Derivatives With Antifungal Activity: A Pharmacophore Model Study," Acta Poloniae Pharmaceutica—Drug Research 65(6):795-798.
Oliver, J.D. et al. (Nov. 8, 2016). "F901318 Represents a Novel Class of Antifungal Drug That Inhibits Dihydroorotate Dehydrogenase," Proc. Natl. Acad. Sci. U.S.A. 113(45):12809-12814.
Plattner, J.J. et al. (Date Unknown). "Medicinal Chemistry of AN2690, A Novel Broad-Spectrum Antifungal Agent in Development for the Topical Treatment of Onychomycosis," Poster #775, Anacor Pharmaceuticals, 1 page.
Pätzel, M. et al. (2005). "Product Class 5: α-Heteroatom-Substituted Alkanamides," Science of Synthesis 21:477-535.
Ribaud, P. et al. (Feb. 1999). "Survival and Prognostic Factors of Invasive Aspergillosis After Allogeneic Bone Marrow Transplantation," Clinical Infectious Diseases 28:322-330.
Rowe, F.M. et al. (1935, e-pub. Jan. 1, 1935). "A Reaction of Certain Diazosulphonates Derived from β-Naphthol-1-Sulphonic Acid. Part XIII. Fission of the Naphthalene Nucleus and Subsequent Closure in Two Directions," Journal of Chemical Society 420:1796-1808.
Rowe, F.M. et al. (1936, e-pub. Jan. 1, 1936). "A Reaction of Certain Diazosulphonates Derived from β-Naphthol-1-Sulphonic Acid. Part XV. Derivatives of 2'-Nitro-4'-Methyl-Benzene-2-Naphthol-1-Diazosulphonate and Synthesis of 2-(2'-Nitro-4'-Methylphenylamino)Isoindolinone-3-Acetio Acid," Journal of Chemical Society 232:1098-1108.
Roy, K. et al. (Dec. 2008). "Development of Linear and Nonlinear Predictive QSAR Models and Their External Validation Using Molecular Similarity Principle for Anti-HIV Indolyl Aryl Sulfones," Journal of Enzyme Inhibition and Medicinal Chemistry 23(6):980-995.
Savage, S.A. et al. (1998). "Efficient Synthesis of 4-, 5-, and 6-Methyl-2,2'-Bipyridine by a Negishi Cross-Coupling Strategy Followed by High-Yield Conversion to Bromo- and Chloromethyl-2,2'-Bipyridines," Journal of Organic Chemistry 63(26):10048-10051.
Schoichet Laboratory at UCSF (through ZINC database of commercially available small molecules- entered to CHEMCATS February and Mar. 2008; p. 1-64.
Scott, M.K. et al., (1995). "Piperazinylalkyl Heterocycles as Potential Antipsychotic Agents," Journal of Medicinal Chemistry 38(21):4198-4210.
Si, Z. et al. (Apr. 6, 2004). "Small-Molecule Inhibitors of HIV-1 Entry Block Receptor-Induced Conformational Changes in the Viral Envelope Glycoproteins," Proceedings of the National Academy of Sciences 101(14):5036-5041.
Slassi, A. et al. (2000). "5-Alkyltryptamine Derivatives as Highly Selective and Potent 5-HT1D Receptor Agonists," Bioorganic & Medicinal Chemistry Letters 10:1707-1709.
Sofan, M.A. et al. (2004). "Studies on 2,3-Dioxopyrrolidines. Synthesis of Piperazine, Pyrrolo[4,5-b]Indole, Pyrazino [5,6-b]Indole and Arylazo Derivatives of Amino Acids," Polish Journal of Chemistry 78:837-842.
Tintelnot, K. et al. (Aug. 2007). "Taxonomic and Diagnostic Markers for Identification of Coccidioides immitis and Coccidioides posadasii," Medical Mycology 45(5):385-393.
Troxler, F. et al. (1968). "Beiträge zur Chemie der Pyrrolo[3,2-c]Azepine und der Pyrrole[3,2-b]Azepine)," Helvetica Chimica Acta 51(8):1870-1880. (English Abstract).
Vecchietti, V. et al. (Jan.-Feb. 1974). "Nitro-Pyrrole Derivatives with Antimicrobial Activity," European Journal of Medicinal Chemistry 9(1):76-80.
Venturella, V.S. (Oct. 1964). "Arylindolizines III. Methoxyl and Glyoxyl Derivatives of Several Substituted Phenylindolizines," Journal of Pharmaceutical Sciences 53(10):1166-1169.
Wahyuningsih, T.D. et al. (2007, e-pub. May 3, 2007). "Synthesis of Indolo[2,3-c]Quinolines From 3-Arylindole-2-Ketoximes," Tetrahedron 63:6713-6719.
Wiederhold, N.P. (2018). "The Orotomide Olorofim (F901318) is Efficacious in a Murine Model of CNS Coccidioidomycosis," Presented at ECCMID Apr. 24, 2018, 14 pages.
Wiederhold, N.P. et al. (2017, e-pub. Mar. 15, 2017). "Dihydroorotate Dehydrogenase Inhibitor F901318 Has Potent in vitro Activity Against Scedosporium Species and Lomentospora prolificans," J Antimicrob. Chermother. 72:1977-1980.
Wiederhold, N.P. et al. (2018, e-pub. Jun. 25, 2018). "The Orotomide Olorofim Is Efficacious in an Experimental Model of Central Nervous System Coccidioidomycosis," Antimicropbial Agents and Chemoterapy 62(9):e00999-18, 7 pages.
Wiederhold, N.P. et al. (Apr. 2018, e-pub. Feb. 5, 2019). "The Novel Fungal Cyp51 inhibitor VT-1598 Is Efficacious in Experimental Models of Central Nervous System Coccidioidomycosis Caused by Coccidioides posadasii and Coccidioides immitis," Antimicropbial Agents and Chemoterapy 62(4):e02258-17, 7 pages.
Yang, Z. et al. (2002). "A Strategy for the Synthesis of Aryl α-Ketoamides Based Upon the Acylation of Anions Derived from Cyanomethylamines Followed by Oxidative Cleavage," Organic Letters 4(7):1103-1105.
Yavari, I. et al. (2001). "Efficient Synthesis of 5,6,7-Trisubstituted 1H-Pyrrolizines," Tetrahedron 57:5873-5878.
Yavari, I. et al. (2002). "A Simple Synthesis of Stable Heterocyclic Phosphorus Ylides Derived from NH-Acids," Phosphorus, Sulfur and Silicon 177:545-553.
Galgiani, J.N. et al. (Nov. 1, 2005). "Coccidioidomycosis," Treatment Guidelines for Coccidioidomycosis 41:1217-1223.
Cacciapuoti, A. et al. (Aug. 2000). "In Vitro and In Vivo Activities of SCH 56592 (Posaconazole), a New Triazole Antifungal Agent, against Aspergillus and Candida," Antimicrobial Agents and Chemotherapy 44(8):2017-2022.
FDA. (Nov. 9, 2006). "Noxafil (Posaconazole) Oral Suspension," retrieved from the Internet https://www.accessdata.fda.gov/drugsatfda_docs/nda/2006/022003s000_NoxafilTOC . . . ., last visited Feb. 12, 2021, 2 pages.
Law, D. et al. (Sep. 2015). "F-759: In Vivo Efficacy of Orally Doses F901318, in a Murine Model of Disseminated Aspergillosis," Poster, 1 page.
Pfaller, M.A. (Oct. 2009, e-pub. Aug. 19, 2009). "Wild-Type MIC Distribution and Epidemiological Cutoff Values for Aspergillus fumigatus and Three Triazoles as Determined by the Clinical and Laboratory Standards Institute Broth Microdilution Methods," Journal of Clinical Microbiology 47(10):3142-3146.
Tacke, D. et al. (2014, e-pub. Jun. 21, 2014). "Primary Prophylaxis of Invasive Fungal Infections in Patients With Haematologic Malignancies. 2014 Update of the Recommendations of the Infectious

(56) References Cited

OTHER PUBLICATIONS

Diseases Working Party of the German Society for Haematology and Oncology," Ann. Hematol. 93:1449-1456.
Yingjin, Y. et al. (Jun. 24, 2021). "Spray Drying Technologies in Search Into Modern Pharmaceutical Preparations," in Modern Pharmaceutical Technology—vol. 2, 10 pages English Translation.
Rajarajan, S. et al. (2009). "Preparation and Evaluation of Ternary Mixing Itraconazole Solid Dispersions by Spray Drying Method," J. Pharm. Sci. & Res. 1(1):22-25.

* cited by examiner

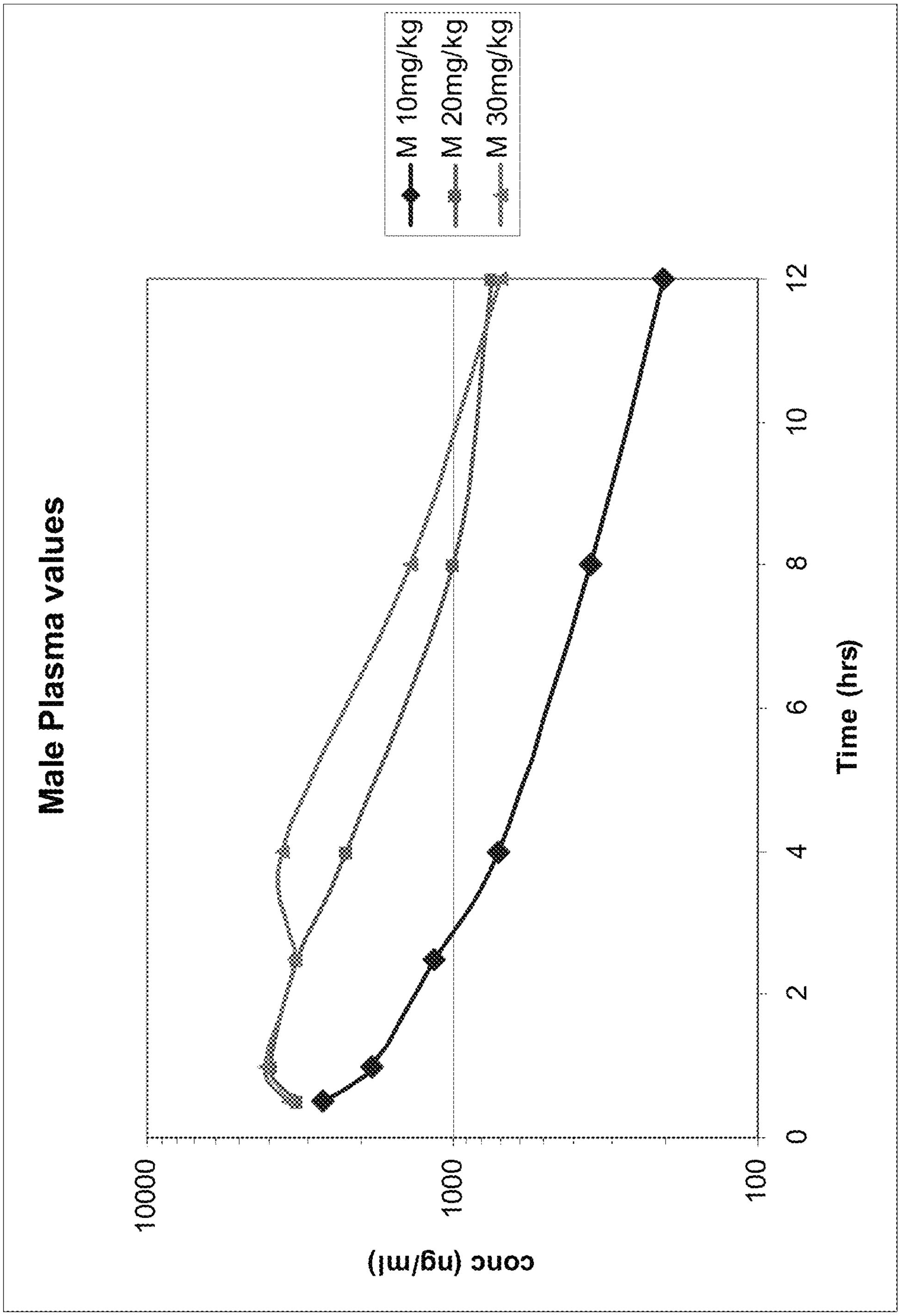
Figure 2 - Continued

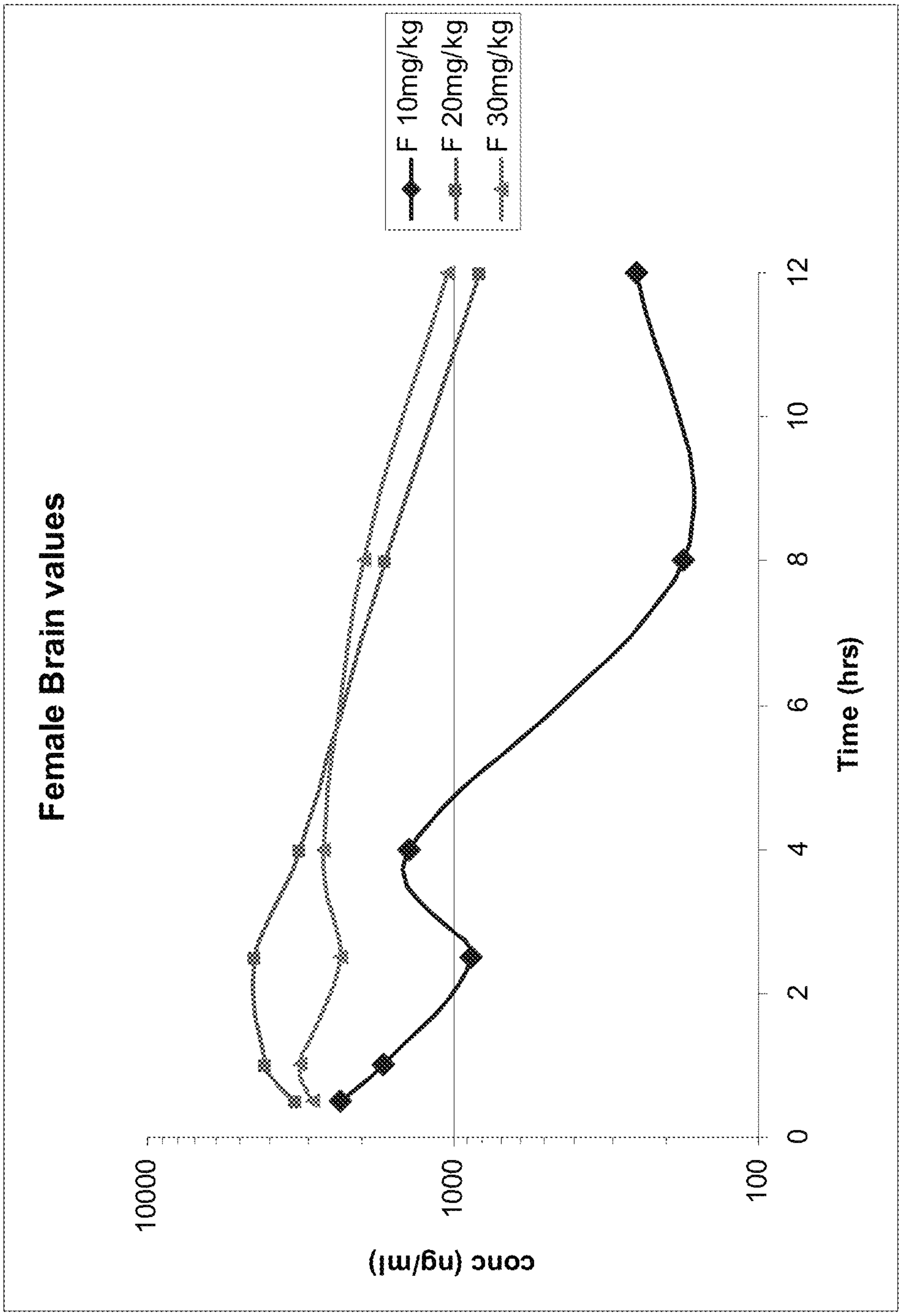
Figure 2 - Continued

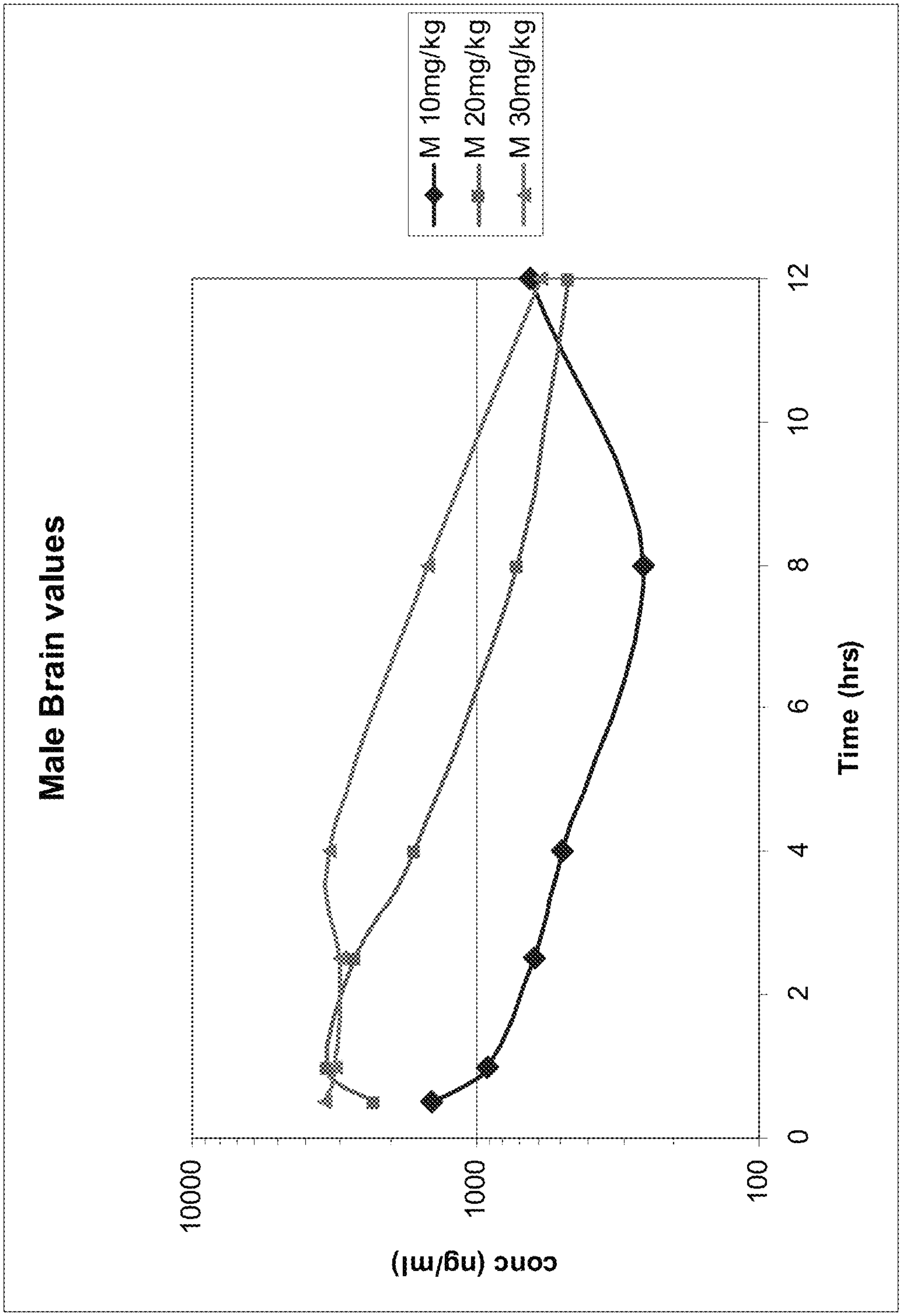
Figure 2 - Continued

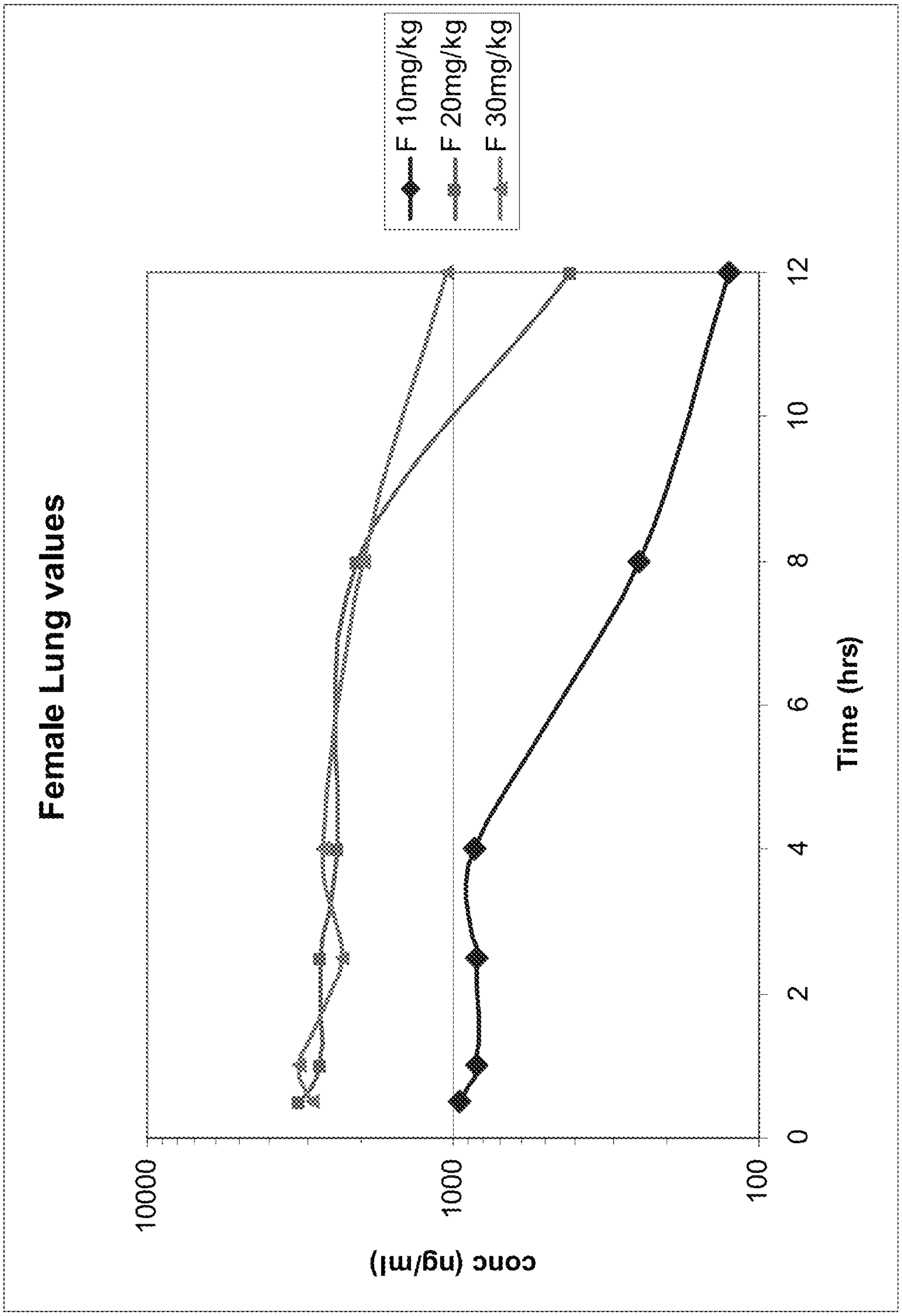
Figure 2 - Continued

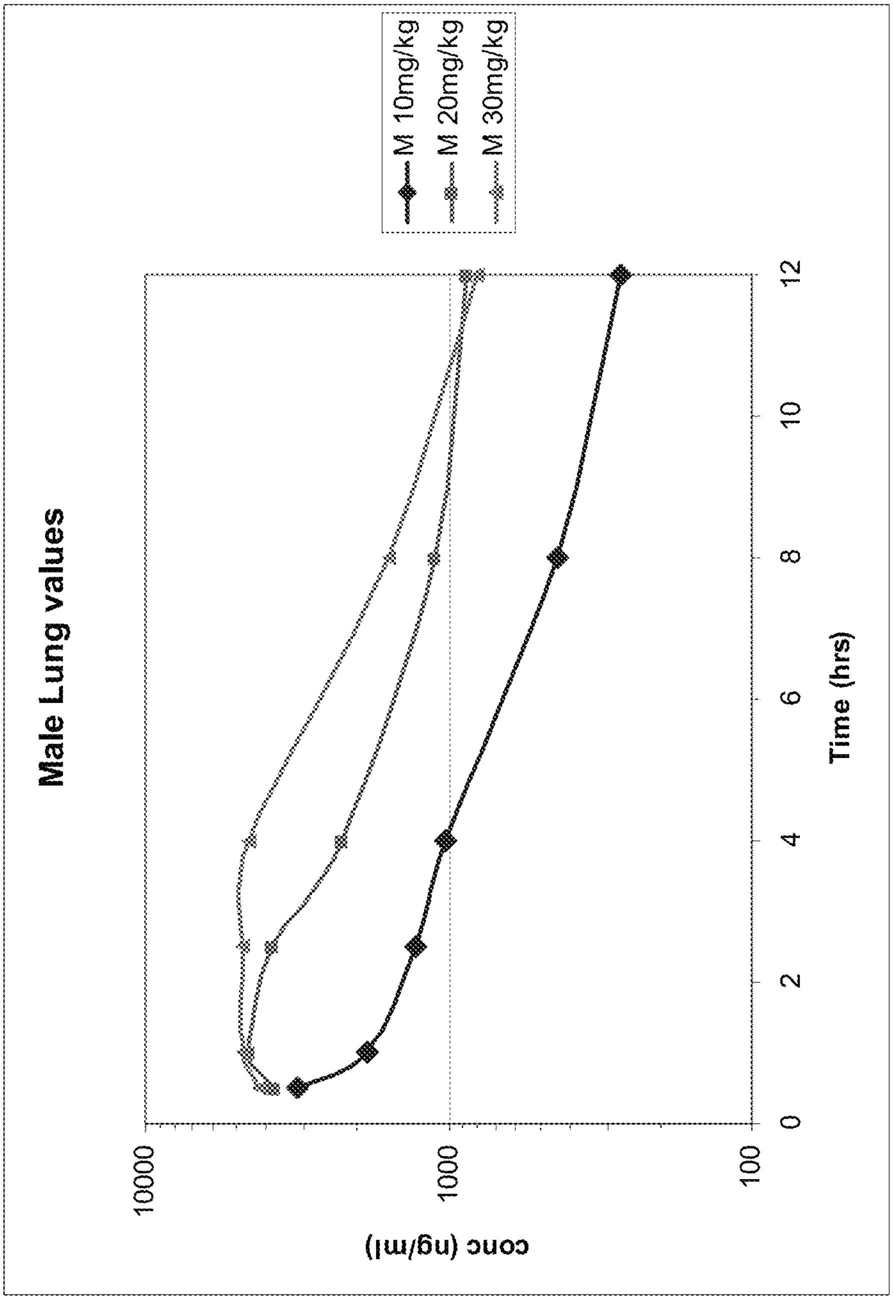
Figure 2 - Continued

METHOD OF TREATING COCCIDIOIDES INFECTION

CROSS-REFERENCE TO RELATED APPLICATIONS

This application claims priority benefit of U.S. Provisional Application No. 62/837,623, filed on Apr. 23, 2019, the disclosure of which is hereby incorporated by reference in its entirety.

FIELD OF THE INVENTION

The invention relates to the therapeutic use of olorofim, 2-(1,5-dimethyl-3-phenyl-1H-pyrrol-2-yl)-N-(4-(4-(5-fluoropyrimidin-2-yl)piperazin-1-yl)phenyl)-2-oxoacetamide, in the prevention and treatment of a fungal infection caused by a *Coccidioides* species.

BACKGROUND

Olorofim (formerly F901318), chemical name 2-(1,5-dimethyl-3-phenyl-1H-pyrrol-2-yl)-N-(4-(4-(5-fluoropyrimidin-2-yl)piperazin-1-yl)phenyl)-2-oxoacetamide, is an agent in a new class of antifungals, the orotomides. Olorofim acts as an inhibitor of the pyrimidine biosynthesis enzyme dihydroorotate dehydrogenase (Oliver J D et al, 2016, F901318 represents a novel class of antifungal drug that inhibits dihydroorotate dehydrogenase. Proc Natl Acad Sci USA 113:12809-12814). Studies have demonstrated that this agent has potent in vitro activity against a variety of molds and endemic fungi (Oliver J D et al, 2016. supra). This agent also has demonstrated potent in vivo activity in murine models of invasive aspergillosis, including infections caused by azole-resistant *Aspergillus fumigatus* (Oliver J D et al, 2016, supra). Inhibition of dihydroorotate dehydrogenase by olorofim appears to be specific to certain fungal species, however, as little to no inhibition occurs in yeast, including *Candida* and *Cryptococcus* species, or against the recombinant human enzyme.

Coccidioidomycosis is a fungal infection that can occur in humans and non-human mammals. This infection is caused by the dimorphic saprobic fungi *Coccidioides immitis* and *Coccidioides posadasii*, which lie dormant in the mycelial form in arid soil. These species are fungi found in warm arid desert regions in the Western Hemisphere, in alkaline sandy soil. Areas in which the species are endemic include areas in Arizona, California, New Mexico, Utah, Nevada, and Texas within the United States, as well as parts of Mexico, Guatemala, Honduras, Venezuela, Brazil, Argentina, and Paraguay. Following inhalation of *Coccidioides* arthroconidia, some infected individuals remain asymptomatic, while others develop mild-to-severe respiratory infections. Disseminated or progressive disease develops in 1 to 3% of infected individuals, and overall morbidity and mortality rates are high among patients with central nervous system (CNS) infections and immunocompromised patients with severe or disseminated disease. Treatment with fluconazole is used for patients with coccidioidal meningitis, due to its excellent safety profile and good penetration into the CNS; therapy must be continued indefinitely, however, as this azole is unable to eradicate the infection. Relapses occur frequently when suppressive therapy is stopped.

Disseminated coccidioidomycosis, especially with CNS involvement, is difficult to treat. Such infections often require lifelong therapy, and CNS coccidioidomycosis is nearly uniformly fatal if left untreated. Current treatment guidelines recommend fluconazole for this purpose. However, fluconazole therapy is suppressive rather than curative for this infectious disease. Lifelong therapy may pose other problems, including toxicities and the potential for drug-drug interactions mediated by inhibition of the cytochrome P450 3A4 enzyme. Although the clinical significance of prolonged fluconazole therapy in the development of resistance in *Coccidioides* species is not fully understood, a recent study reported an increase in the number of *Coccidioides* isolates with reduced in vitro susceptibility to fluconazole, thus raising concerns regarding potential resistance to this azole. Resistance following prolonged therapy has been reported in the literature, although the clinical data are limited.

There is, therefore, a need for an improved therapy that offers an alternative to the presently preferred fluconazole therapy. Any new therapy should provide safe and effective treatment for fungal infections caused by *Coccidioides* species, and seek to avoid the need for long-term suppressive treatment with the associated risks of increased toxicity and negative drug-drug interactions.

SUMMARY OF THE INVENTION

Olorofim (2-(1,5-dimethyl-3-phenyl-1H-pyrrol-2-yl)-N-(4-(4-(5-fluoropyrimidin-2-yl)piperazin-1-yl)phenyl)-2-oxoacetamide) has been shown to exhibit potent in vitro activity against both *Coccidioides immitis* and *Coccidioides posadasii*. Studies detailed herein have demonstrated that 2-(1,5-dimethyl-3-phenyl-1H-pyrrol-2-yl)-N-(4-(4-(5-fluoropyrimidin-2-yl)piperazin-1-yl)phenyl)-2-oxoacetamide can provide reductions in brain tissue fungal burdens during treatment. Surprisingly, fungal burdens have remained low both during treatment and after cessation of treatment (i.e., no rebound effect is observed).

Olorofim selectively inhibits the de novo pyrimidine biosynthesis of filamentous fungi by targeting dihydroorotate dehydrogenase (DHODH) (Oliver J D et al, 2016. supra). DHODH is an oxidoreductase that catalyses the fourth step of the pyrimidine biosynthesis pathway, the conversion of dihydroorotate to orotate. The pyrimidines uracil, thymine and cytosine are building blocks of DNA and RNA, thus inhibition of their synthesis is likely to have multiple effects, including affecting cell cycle regulation and protein synthesis. Additionally, uridine-5'-triphosphate (UTP) is required for the formation of uridine-diphosphate glucose (UDP-glucose), which is an important precursor for several cell wall components.

Whilst not being bound by theory, the in vivo activity of 2-(1,5-dimethyl-3-phenyl-1H-pyrrol-2-yl)-N-(4-(4-(5-fluoropyrimidin-2-yl)piperazin-1-yl)phenyl)-2-oxoacetamide appears to be independent of the peak concentration of the therapeutic agent in blood plasma. This is consistent with the mechanism of action, which is effectively a starvation mechanism, providing very low pyrimidine levels in the fungal cell. This results in the cell being unable to produce DNA and RNA and to undergo protein synthesis when olorofim is present. Particular advantages are achieved with an administration regime providing olorofim in an amount sufficient to keep exposure above the level required to maintain pyrimidine starvation in the fungal cell of *Coccidioides* species.

2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may be used in a method of treating or preventing a fungal infection in a subject, wherein the infection is caused by a *Coccid-*

*ioides* species, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof.

The invention provides a method of treating or preventing a fungal infection in a subject, wherein the infection is caused by a *Coccidioides* species, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject at least twice daily, for example, at least three times daily.

Also provided by the invention is a method of treating or preventing a fungal infection in a subject, wherein the infection is caused by a *Coccidioides* species, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, wherein pyrimidine starvation in *Coccidioides* cells in said subject is maintained for the duration of treatment.

The invention also provides a method of treating or preventing a fungal infection in a subject, wherein the infection is caused by a *Coccidioides* species, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, wherein the subject's fungal burden remains suppressed after cessation of treatment.

Also provided by the invention is a method of treating or preventing disseminated coccidioidomycosis, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof.

DETAILED DESCRIPTION OF THE INVENTION

Figure 1:
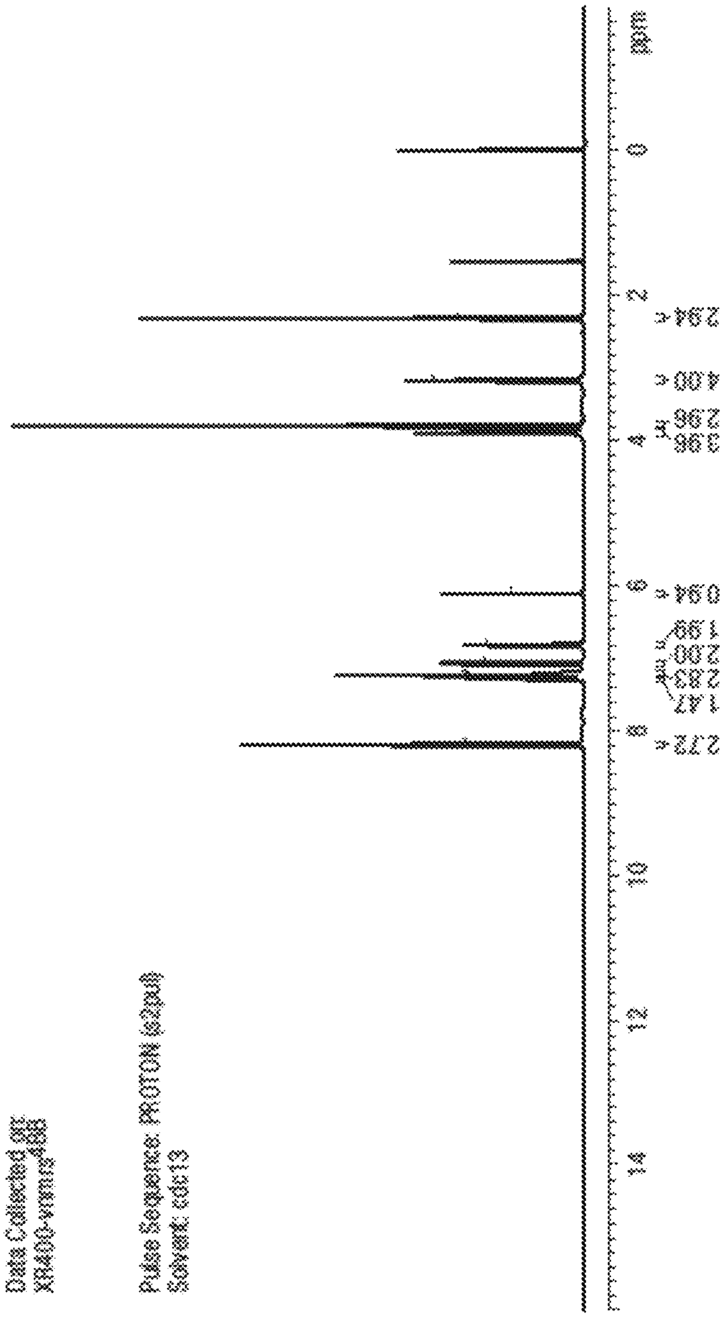
FIG. 1 provides NMR data for 2-(1,5-Dimethyl-3-phenyl-1H-pyrrol-2-yl)-N-{4-[4-(5-fluoro-pyrimidin-2-yl)-piperazin-1-yl]-phenyl}-2-oxo-acetamide ($^1H$ NMR (400 MHz, $CDCl_3$)).

The methods of the invention require administration to a subject of an effective amount of the therapeutic agent 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof. The chemical structure of 2-(1,5-dimethyl-3-phenyl-1H-pyrrol-2-yl)-N-(4-(4-(5-fluoropyrimidin-2-yl)piperazin-1-yl)phenyl)-2-oxoacetamide is:

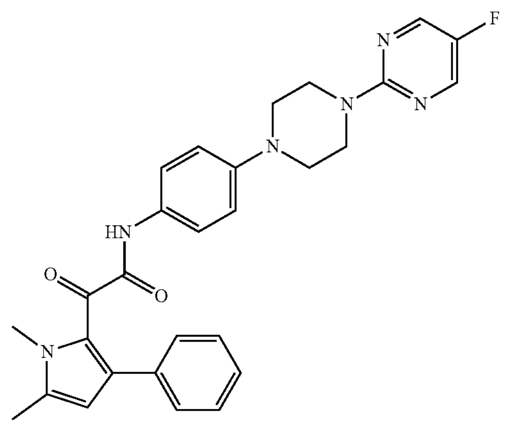 [SMILES: Cc1cc(-c2ccccc2)c(C(=O)C(=O)Nc2ccc(N3CCN(c4ncc(F)cn4)CC3)cc2)n1C]

2-(1,5-dimethyl-3-phenyl-1H-pyrrol-2-yl)-N-(4-(4-(5-fluoropyrimidin-2-yl)piperazin-1-yl)phenyl)-2-oxoacetamide was formally identified by the reference number F901318 and is known by the name olorofim. A reference to either F901318 or olorofim is, therefore, a reference to 2-(1,5-dimethyl-3-phenyl-1H-pyrrol-2-yl)-N-(4-(4-(5-fluoropyrimidin-2-yl)piperazin-1-yl)phenyl)-2-oxoacetamide.

2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may be used in a method of treating or preventing a fungal infection in a subject, wherein the infection is caused by a *Coccidioides* species, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, i.e., olorofim, or a pharmaceutically acceptable salt thereof.

As discussed above, olorofim has been shown to provide in vivo activity against *Coccidioides* species. The *Coccidioides* species may be *Coccidioides immitis* and/or *Coccidioides posadasii*. As used herein, the term *Coccidioides* species also extends to azole-resistant *Coccidioides* isolates. The methods of the invention may, for example, be used in the treatment and prevention of a fungal infection caused by *Coccidioides immitis* and/or *Coccidioides posadasii*, for example *Coccidioides immitis*.

*Coccidioides* (i.e., *Coccidioides immitis* or *Coccidioides posadasii*) infection causes coccidioidomycosis. Coccidioidomycosis typically begins in an acute form (sometimes referred to as pulmonary coccidioidomycosis), that may progress to a chronic form (chronic coccidioidomycosis) and then to disseminated coccidioidomycosis (which includes primary cutaneous coccidioidomycosis).

Olorofim (2-(1,5-dimethyl-3-phenyl-1H-pyrrol-2-yl)-N-(4-(4-(5-fluoropyrimidin-2-yl)piperazin-1-yl)phenyl)-2-oxoacetamide), or a pharmaceutically acceptable salt thereof, may be used to treat all forms of coccidioidomycosis. Thus, the methods of the invention may comprise the treatment and prevention of coccidioidomycosis, for example, acute coccidioidomycosis, chronic coccidioidomycosis or disseminated coccidioidomycosis.

Coccidioidal meningitis is a severe form of coccidioidomycosis. 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may be used to treat or prevent coccidioidal meningitis.

In some embodiments, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is used to treat or prevent disseminated coccidioidomycosis. Olorofim, or a pharmaceutically acceptable salt thereof, may, for example, be used to treat patients with central nervous system (CNS) infections (CNS coccidioidomycosis). Patients treated with olorofim, or a pharmaceutically acceptable salt thereof, may, for example, be immuno-compromised patients.

The subject may be a human or a non-human mammal. Where the subject is non-human mammal, the subject may be a domesticated, captive or wild animal, for example, a dog, cat, horse, ruminant (e.g., cattle, sheep or llama) or pig. Typically the subject is human.

The rate at which olorofim, or a pharmaceutically acceptable salt thereof, is metabolised in a subject may depend upon whether the subject is human or a non-human mammal. For example, mice metabolise olorofim more rapidly than humans.

Several risk factors for severe or disseminated infection have been identified. The methods of the invention may be used to treat or prevent an infection caused by a *Coccidioides* species in a subject having at least one of these risk factors. These risk factors include: Filipino or African ethnicity, HIV/AIDS, pregnancy, and cardiopulmonary disease. Other subjects at risk of an infection caused by a *Coccidioides* species include diabetic patients with poor glycemic control (blood glucose>220 mg/dL); subjects taking immunosuppressive medications, including corticosteroids, tumor necrosis factor-α inhibitors, and calcineurin inhibitors; subjects with impaired T-cell function, including subjects with hematologic malignancies, especially non-Hodgkin's lymphoma and chronic lymphocytic leukemia, and subjects with inflammatory arthritis. In endemic areas, coccidioidomycosis is also a serious infectious complication in patients undergoing organ transplantation.

There are also occupational risk groups, e.g., farmers, construction workers and archaeologists, encompassing subjects most likely to come into contact with *Coccidioides* species.

Coccidioidomycosis is also seasonal, with the weather a driving factor in when incidents peak. Rain promotes growth of mycelia and epidemics may occur when drought or winds follow a period of heavy rain.

*Coccidioides* species are propagated by arthroconidia (arthospores) and endospores. Infection to human and non-human mammals typically occurs via inhalation of *Coccidioides* arthroconidia.

2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may prevent inhaled *Coccidioides* arthroconidia from causing infection, and thus may be used in a method of preventing a fungal infection in a subject, wherein the infection is caused by a *Coccidioides* species.

Symptoms of coccidioidomycosis infection are typically observed from one to three weeks after exposure to *Coccidioides* arthroconidia.

In one embodiment, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to a subject considered to be at risk of infection. 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may be administered prior to or shortly after exposure to *Coccidioides* arthroconidia. The subject may have any one, or more than one, of the risk factors as identified herein. Preventative treatments may, for example, be provided to a subject having at least one risk factor as identified herein during periods of drought or winds following a period of heavy rain.

Olorofim may, additionally and/or alternatively, be administered to a subject prior to exposure to *Coccidioides* arthroconidia. Such preventative treatment may, for example, be provided to a subject travelling to or staying in a geographical area where *Coccidioides immitis* and/or *Coccidioides posadasii* are endemic (e.g., Arizona, California, New Mexico, Utah, Nevada, and Texas within the United States, as well as parts of Mexico, Guatemala, Honduras, Venezuela, Brazil, Argentina, and Paraguay).

In one embodiment, olorofim, or a pharmaceutically acceptable salt thereof, may be administered to a subject shortly after exposure to *Coccidioides* arthroconidia (e.g., before the subject exhibits any symptoms of coccidioidomycosis) to prevent the subject developing coccidioidomycosis, for example, developing acute coccidioidomycosis, chronic coccidioidomycosis or disseminated coccidioidomycosis. The olorofim, or a pharmaceutically acceptable salt thereof, may, for example, be administered less than 21 days after the subject is exposed to *Coccidioides* arthroconidia, for example, less than 14 days after the subject is exposed to *Coccidioides* arthroconidia, e.g., less than 7 days of the subject being exposed to *Coccidioides* arthroconidia. The olorofim may, for example, be administered one, two, three, four or five days after the subject is exposed to *Coccidioides* arthroconidia, e.g., one, two or three days after the subject is exposed to *Coccidioides* arthroconidia.

As mentioned above, if left untreated disseminated coccidioidomycosis is often fatal. Olorofim may, therefore, advantageously be used to prevent an initial coccidioidomycosis infection spreading or disseminating outside of the lungs (e.g., to skin, bones, liver, brain, heart, and the membranes that protect the brain and spinal cord), i.e., to prevent an acute form of coccidioidomycosis developing into chronic coccidioidomycosis or disseminated coccidioidomycosis. In such cases, olorofim should be administered to the subject as soon as possible after the initial symptoms of coccidioidomycosis occur, for example, within 28 days of the initial symptoms, e.g., with 21, 14 or 7 days of the initial symptoms. Such symptoms include, but are not limited to, cough (e.g., producing phlegm/mucus or blood), fatigue, fever, headache, muscle aches, rash, joint pain and/or swelling (tender bumps usually on the leg(s)).

In one embodiment, the invention provides a method of treating or preventing a fungal infection in a subject, wherein the infection is caused by a *Coccidioides* species, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, wherein pyrimidine starvation in *Coccidioides* cells in said subject is maintained for the duration of treatment.

As used herein, "treatment" or "treating" is an approach for obtaining a beneficial or desired result, such as a clinical result. For purposes of this invention, beneficial or desired clinical results include, but are not limited to, alleviation of a symptom and/or diminishment of the extent of a symptom and/or preventing a worsening of a symptom associated with and/or preventing recurrence of a fungal infection caused by a *Coccidioides* species, such as *Coccidioides immitis* and/or *Coccidioides posadasii*. In one variation, beneficial or desired clinical results include, but are not limited to, alleviation of a symptom and/or diminishment of the extent of a symptom and/or preventing a worsening of a symptom associated with a fungal infection caused by a *Coccidioides* species. Thus, it is understood that treatment in one aspect includes reducing the fungal burden in a subject, such as reducing the fungal burden in a subject having coccidioidomycosis.

As used herein, "preventing" a fungal infection caused by a *Coccidioides* species means to postpone development of the fungal infection over a period of time such that the subject does not develop the fungal infection. In some variations, the subject does not develop the fungal infection for at least 1 month, for example 3, 6, 9, or 12 months. Prevention may be contemplated in one aspect in a subject at risk of developing a fungal infection caused by a *Coccidioides* species.

As used herein, pyrimidine starvation is present in a cell when the cell is unable to effectively synthesise pyrimidine-DNA or RNA. Pyrimidine starvation typically occurs where the drug concentration in the subject's blood plasma is maintained at 250 ng/ml or over.

As mentioned herein, olorofim, or 2-(1,5-dimethyl-3-phenyl-1H-pyrrol-2-yl)-N-(4-(4-(5-fluoropyrimidin-2-yl)piperazin-1-yl)phenyl)-2-oxoacetamide, is an analog of the orotomide class of drugs that inhibits fungal pyrimidine biosynthesis. More specifically, olorofim acts as an inhibitor of the pyrimidine biosynthesis enzyme dihydroorotate dehydrogenase (DHODH). An effective amount of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is sufficient to provide continuous inhibition of the pyrimidine biosynthesis enzyme dihydroorotate dehydrogenase for the duration of treatment.

As the person skilled in the art will appreciate, the amount of a given therapeutic agent in a subject's blood may vary between doses of the therapeutic agent. The trough level, sometimes referred to as the trough concentration or Cmin, is the lowest concentration reached by a therapeutic drug in a patient (e.g., in a patient's blood) between doses. This will typically be measured just prior to administration of the therapeutic drug. In contrast, the peak level, or peak concentration or Cmax, is the highest concentration reached by a therapeutic drug in a patient's blood. This typically occurs shortly after dosing, e.g., within one or two hours of dosing, depending upon the active agent used. Monitoring of peak and/or trough levels is widely used, for example, in clinical trials to provide information on the efficacy and safety of a therapeutic agent, and the skilled person would be aware of techniques suitable to measure both peak and trough levels.

In order to maintain pyrimidine starvation in the fungal cell of *Coccidioides* species in said subject the administration of olorofim should be sufficient to maintain Cmin (the minimum blood plasma concentration reached by a drug prior to administration of a further dose) at or above the level required to maintain pyrimidine starvation in the fungal cell of *Coccidioides* species, i.e., to provide continuous inhibition of the pyrimidine biosynthesis enzyme dihydroorotate dehydrogenase, for the duration of treatment.

Cmin may, for example, be maintained at or above 250 ng/ml of olorofim in said subject's blood plasma, for example, at or above 500 ng/ml, 600 ng/ml or 700 ng/ml of olorofim in said subject's blood plasma.

Thus, in some embodiments Cmin is maintained at at least 250 ng/ml of olorofim in said subject's blood plasma, for example, at least 500 ng/ml, 600 ng/ml or 700 ng/ml of olorofim in said subject's blood plasma.

In one embodiment Cmin is maintained at between 1 and 750 ng/ml, for example, 2 and 600 ng/ml, e.g., 3 and 500 ng/ml.

In one embodiment, the MIC (minimum inhibitory concentration) for olorofim, or a pharmaceutically acceptable salt thereof, is less than or equal to 0.1 μg/ml, for example, less than or equal to 0.06 μg/ml. The MIC may, for example, be from 0.001 to 0.1 μg/ml, for example, from 0.008 to 0.06 μg/ml. In one embodiment, the $MIC_{50}$ for olorofim, or a pharmaceutically acceptable salt thereof, is less than or equal to 0.01 μg/ml, for example, less than or equal to 0.008 μg/ml and/or the $MIC_{90}$ for olorofim, or a pharmaceutically acceptable salt thereof, is less than or equal to 0.02 μg/ml, for example, less than or equal to 0.015 μg/ml. In some embodiments the geometric mean (GM) MIC for olorofim, or a pharmaceutically acceptable salt thereof, is less than or equal to 0.02 μg/ml, for example, less than or equal to 0.01 μg/ml, e.g., about 0.011 μg/ml or about 0.009 μg/ml. The MIC values may be obtained, for example, by broth macrodilution as described herein in the examples section.

Typically, in order to maintain pyrimidine starvation, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, should be at a preferred dosing frequency and/or amount. Thus, in some embodiments 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered more than once a day, for example, at least two, three, four or five times daily. In some embodiments it is administered, at least three times daily, for example, three or four times daily, e.g., three times daily.

As mentioned above, the rate at which olorofim, or a pharmaceutically acceptable salt thereof, is metabolised in a subject may depend upon whether the subject is human or a non-human mammal. The preferred dosing frequency and/or amount may, therefore, differ in different types of subject. For example, the preferred dosing frequency and/or amount may be different in human and non-human subjects.

In some embodiments, over the course of one day of treatment, the dose (i.e. the total daily dose) of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject may, for example, be 2 to 50 mg/kg/d of body weight, e.g., 20 to 50 mg/kg/d of body weight. The total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject may, for example, be about 40 mg/kg/d of body weight, about 20 mg/kg/d of body weight or about 2 mg/kg/d of body weight.

In some embodiments, each individual dose administered to the subject in a day is the same amount. Thus, each individual dose administered in a day is equal to the total daily dose divided by the number of individual doses in that day. By way of some examples, (i) when the total daily dose is 2 mg/kg/d and olorofim, or a pharmaceutically acceptable salt therefore, is administered three times daily, each individual dose would be 0.67 mg and (ii) when the total daily dose is 50 mg/kg/d and olorofim, or a pharmaceutically acceptable salt therefore, is administered three times daily, each individual dose would be 16.67 mg.

In other embodiments, the individual doses administered to the subject in the day may vary, i.e., not all doses in a given day are the same. When, for example, three doses are administered to the patient in a day, (a) all three doses may be different amounts or (b) the subject may be administered with two doses of equal amounts and one dose that is either more or less than the other two doses, wherein the one dose that is either more or less than the other two doses may be the first, second or third dose of the day.

The term “duration of treatment” as used herein refers to the treatment of a single episode of a fungal infection caused by a *Coccidioides* species. Thus, for example, if a patient were to recover completely from a first episode of a fungal infection caused by a *Coccidioides* species and then later succumb to a separate second episode of a fungal infection caused by a *Coccidioides* species the duration of treatment applies to treatment of only the first episode or only the second episode and not the treatment of both the first and the second episode.

The duration of treatment or treatment period (the length of time over which doses of the therapeutic agent are provided to the subject) will vary depending upon a number of factors including the severity of the fungal infection. Typically, the duration of treatment is from one day to one year (365 days), more typically from one day to six months, e.g., from one week to six months, for example, from three months to six months.

In some embodiments, the treatment period is at least three months.

As discussed herein, fungal infections caused by *Coccidioides* species are presently preferably treated using fluconazole therapy. This treatment is suppressive rather than curative. The methods of the prevent invention aim to provide an improved therapy that cures the fungal infection, i.e., prevents or avoids recurrence of infection after a course of treatment has ended.

The presence and severity of a fungal infection in a subject may be monitored by assessing the fungal burden in the subject. As used herein, fungal burden is a count of the number of fungal cells in a sample. Fungal burden may be measured in tissue, blood, or plasma for example. Fungal burden in a subject may, for example, be measured by determining the fungal cell count in the subject’s blood plasma.

Additionally or alternatively, markers of fungal infection may be used to assess the presence and severity of a fungal infection in a subject. For example, measurement of *Coccidioides* antigen or *Coccidioides* antibodies may be used to determine the level and/or extent of infection. These markers may, for example, be used as a measure of the fungal burden in the subject’s brain tissue and/or lung tissue.

An effective treatment of a fungal disease may provide a reduction in fungal burden during the treatment period. An effective treatment of a fungal disease may also provide a reduction in *Coccidioides* antigen and/or *Coccidioides* antibodies over time. The antibodies may, for example, be antibodies to *Coccidioides immitis* antigens and/or antibodies to *Coccidioides posadasii* antigens. The antigens may, for example, be antigens of *Coccidioides immitis* and/or *Coccidioides posadasii.*

When the treatment is purely suppressive in nature, the fungal burden in the subject will rebound once dosing with the therapeutic agent is stopped. The fluconazole therapy presently used to treat fungal infections caused by a *Coccidioides* species is a suppressive therapy. When closing with fluconazole is stopped a rebound in fungal burden is observed. Suppressive treatments require life-long dosing, which is not only burdensome on the patient and reliant on the subject maintaining treatment over a long period of time, but can also be associated with higher risk of toxicity of the therapeutic agent in the patient, negative drug-drug interactions between the therapeutic agent of the suppressive treatment and other therapeutic agents required, and a potential for development of resistance, in this case resistance in *Coccidioides* species. Given this, it would be preferable if no rebound effect were observed after dosing with a therapeutic agent has stopped.

Treatment with olorofim or a pharmaceutically acceptable salt thereof is effective in delaying or preventing a rebound in fungal burden after dosing has stopped. The invention therefore also provides a method of treating or preventing a fungal infection in a subject, wherein the infection is caused by a *Coccidioides* species, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, wherein the effective amount is sufficient to suppress fungal burden after cessation of treatment. The fungal burden may, for example, be the fungal burden as measured in the subject’s blood plasma.

Fungal burden may be determined from the number of colony-forming units (CFUs) per millilitre of blood plasma. Additionally or alternatively, fungal burden may be assessed by monitoring the titre of antigen or antibody in the blood or plasma.

Fungal burden can be obtained by aliquoting a known volume of blood, plasma or serum onto a fungal growth media such as Potato dextrose agar, malt extract agar or Sabouraud dextrose agar. It may be necessary to pre-dilute the sample prior to aliquoting onto the growth media. Fungal burden is obtained by counting the number of fungal colonies growing on the growth media and attributing that number to the volume of material added. This assumes that each fungal colony is derived from a single fungal cell in the tissue or blood/plasma. Accuracy may be reduced if fungal cells aggregate together so that multiple fungal cells form a single colony. If a pre dilution step is needed then this is taken into consideration. For example, if the sample is diluted 1 in 10, then the number of colonies is calculated by:

$$\text{Colony number} \times \text{volume} \times \text{dilution} \quad (10).$$

Similarly, fungal burden can be determined in tissue where a known mass of tissue is homogenised in a known volume of buffer or fluid. Here, the fungal burden is calculated back to the mass of the tissue.

Although the accuracy can be variable, this variability is constant through successive fungal burden estimates allowing comparison.

The fungal burden may be suppressed for at least 7 days, for example, for at least 14 days, at least 21 days or at least 28 days, after cessation of treatment. In some embodiments, the fungal burden is suppressed for at least 1 month, for example 3, 6 or 9 months after cessation of treatment. In some embodiments, the fungal burden is suppressed for at least 1 year after cessation of treatment.

Typically, the subject does not exhibit a rebound in fungal burdens after cessation of treatment. A rebound effect is observed when the number of CFUs per millilitre of blood plasma increases after cessation of treatment. Thus, typically, the subject does not exhibit an increase in the number of CFUs per millilitre of blood plasma after cessation of treatment. Put another way, after the final dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is provided to the patient the number of CFUs per millilitre of blood plasma preferably does not increase, i.e., the number of CFUs per millilitre of blood plasma typically reduces or stays the same. CFUs may be difficult to measure with absolute accuracy, and thus small increases (for example, no more than 20%, e.g., no more than 10%) in the number of CFUs per millilitre of blood plasma may be observed after cessation of treatment.

Commercial assays are available to measure antigens from *Coccidioides* species or human serum antibody titres. These commercial diagnostic tests can be used to monitor serum markers of infection. Decreases in serum marker levels can be considered to suggest that an infection is retreating. Serum marker levels which return to normal or antigen levels which are negative can be considered to indicate an infection is no longer active.

Examples of cocci antigen/antibody tests include, but are not limited to, the MiraVista Diagnostics MVista® *Coccidioides* Quantitative Ag EIA (antigen test); the *Coccidioides* Antigen (IDTP) for Immunodiffusion (ID) Test Immy; the s ōna *Coccidioides* Antibody Lateral Flow Assay (LFA) (which may be used for the qualitative detection of serum antibodies directed against TP and CF antigens from *Coccidioides* species); and the IMMY *Coccidioides* Antibody Enzyme Immunoassay.

In one embodiment, the fungal burden is suppressed when serum marker levels return to normal and/or antigen levels are negative.

The invention also provides a method of treating or preventing a fungal infection in a subject, wherein the infection is caused by a *Coccidioides* species, which method comprises: administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, wherein the subject's serum marker levels return to normal and/or antigen levels are negative after cessation of treatment.

Typically, in the methods of the invention, when the subject does not exhibit a rebound in fungal burdens after cessation of treatment, said subject will exhibit no further symptoms connected to coccidioidomycosis (acute, chronic or disseminated coccidioidomycosis) and/or there is no development of the coccidioidomycosis (e.g., acute or chronic coccidioidomycosis) to disseminated coccidioidomycosis. Thus, the subject is no longer suffering from a fungal infection caused by a *Coccidioides* species.

Cessation of treatment is the point at which the final dose, in the course of treatment, is administered. Treatment may, for example, be stopped when said subject exhibits no further symptoms connected to coccidioidomycosis (acute, chronic or disseminated coccidioidomycosis). Thus treatment may be stopped when the subject is no longer suffering from a fungal infection caused by a *Coccidioides* species. In some embodiments, cessation of treatment occurs after the subject has been treated for between one day and one year (365 days), for example, between one day and six months. In some embodiments, cessation of treatment occurs after the subject has been treated for between three months to six months. In some embodiments, cessation of treatment occurs after the subject has been treated for at least three months.

Markers of infection such as serum antigens may present as repeatedly negative over a period of several months. Similarly, antibody titres to *Coccidioides* may fall and stay low. Thus, in some embodiments, treatment may be stopped when markers of infection such as serum antigens present as negative for at least two months, for example, for at least three, four, five or six months. Additionally or alternatively, treatment may be stopped when antibody titres to *Coccidioides* remain low for at least two months, for example, for at least three, four, five or six months.

After cessation of treatment, typically, serum antigens present as repeatedly negative over a period of at least one month, for example, at least two, three, four, five or six months. Additionally or alternatively, antibody titres to *Coccidioides* remain low for least one month, for example, at least two, three, four, five or six months after cessation of treatment. Thus, the markers of infection may be used to demonstrate no rebound effect in the subject. In one embodiment antibody titres to *Coccidioides* remain at normal (low) level least one month, for example, at least two, three, four, five or six months after cessation of treatment. Normal serum marker levels are levels in the range expected for a subject without an infection (i.e., without an infection caused by a *Coccidioides* species).

As the person skilled in the art will appreciate, the treatment period (the length of time over which doses of the therapeutic agent are provided to the subject) will vary depending upon a number of factors include the severity of the fungal infection. Typically, the treatment period is from one day to one year (365 days), for example, from one day to six months, for example, from one week to six months, for example, from three months to six months.

In some embodiments, the treatment period is at least three months.

In some embodiments, provided herein is a method of reducing fungal burden in a subject having an infection which is caused by a *Coccidioides* species, which method comprises administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof. In some embodiments, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject at least twice daily, for example at least three times daily. In some embodiments, the method comprises administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide. In some embodiments, a total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject is from 2 to 50 mg/kg. In some embodiments, the *Coccidioides* species is *Coccidioides immitis* and/or *Coccidioides posadasii.* In some embodiments, the subject is suffering from or susceptible to coccidioidomycosis. In some embodiments, the coccidioidomycosis is disseminated coccidioidomycosis. In some embodiments, the 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject orally. In some embodiments, the method comprises administration to said subject of a pharmaceutical composition comprising an effective amount of 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof, together with one or more pharmaceutically acceptable carriers and/or excipients. In some embodiments, the method comprises administration to said subject of a pharmaceutical combination comprising: (i) 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof, and (ii) a second antifungal agent such as fluonazole.

In some embodiments, provided herein is a method of administering 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, to a subject, wherein the subject has an infection which is caused by a *Coccidioides* species.

Solvates and Tautomeric Forms

For the avoidance of doubt, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or the pharmaceutically acceptable salt thereof can, if desired, be used in the form of a solvate. Further, for the avoidance of doubt, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or the pharmaceutically acceptable salt thereof may be used in any tautomeric form.

Pharmaceutically Acceptable Salts

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic, hydroiodic or nitric acid and organic acids such as citric, fumaric, maleic, malic, ascorbic, succinic, tartaric, benzoic, acetic, methanesulphonic, ethanesulphonic, benzenesulphonic, p-toluenesulphonic acid, formic, acetic, propionic, glycolic, lactic, pyruvic, oxalic, salicylic, trichloroacetic, picric, trifluoroacetic, cinnamic, pamoic, malonic, mandelic, bismethylene salicylic, ethanedisulfonic, gluconic, citraconic, aspartic, stearic, palmitic, EDTA, p-aminobenzoic or glutamic acid, sulfates, nitrates, phosphates, perchlorates, borates, acetates, benzoates, hydroxynaphthoates, glycerophosphates or ketoglutarates. Further examples of pharmaceutically acceptable inorganic or organic acid addition salts include the pharmaceutically acceptable salts listed in Journal of Pharmaceutical Science, 66, 2 (1977) which are known to the skilled artisan. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines, lysine, guanidine, diethanolamine and choline.

Also intended as pharmaceutically acceptable acid addition salts are the hydrates which the present compound is able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may form solvates with standard low molecular weight solvents using methods known to the skilled artisan.

Prodrug

A prodrug of 2-(1,5-dimethyl-3-phenyl-1H-pyrrol-2-yl)-N-(4-(4-(5-fluoropyrimidin-2-yl)piperazin-1-yl)phenyl)-2-oxoacetamide may be used in the methods of the invention. The prodrug may, for instance, provide enhanced solubility, permeability, adsorption, distribution and formulation, and/or lower toxicity.

A prodrug is an analogue of 2-(1,5-dimethyl-3-phenyl-1H-pyrrol-2-yl)-N-(4-(4-(5-fluoropyrimidin-2-yl)piperazin-1-yl)phenyl)-2-oxoacetamide which will be converted in vivo to the desired active compound. Suitable methods will be known to those skilled in the art.

Particularly suitable prodrugs include those in which a nitrogen atom of the compound is quaternised by addition of an ester or alkyl ester group. For example, the nitrogen atom of an amine group may be quaternised by addition of a $—CH_2—O—COR$ group, wherein R is typically methyl or tert-butyl.

Other suitable prodrugs include those in which a moiety is added to the phenyl ring adjacent to the piperazinyl group. Relative to the amide (—NH—CO—) moiety, the moiety may be added to the phenyl ring at the ortho or meta position, preferably at the meta position. The prodrug may, for instance, have the general formula:

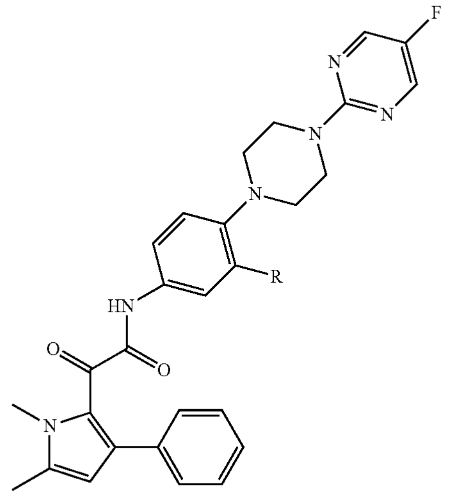

wherein R is a group of formula $—O—CO—OR^1$, $—O—CO—R^1$, $—O—CO—NR^1R^2$, $—O—CO—(CH_2)_z—NR^1R^2$, $—OR^1$, $—O—(CR^{11}R^{12})_z—O—CO—R^3$-, $—O—P(O)(OR^4)(OR^5)$ or $—O—(CH_2)_z—O—P(O)(OR^4)(OR^5)$, wherein: $R^1$, $R^2$ and $R^3$ are independently hydrogen, C1-C4 alkyl, C2-C4 alkenyl, C2-C4 alkynyl, C3-C6 cycloalkyl, an unsubstituted 5- to 7-membered heterocyclyl group, or a 5- to 7-membered heterocyclyl group substituted with up to three substituents selected from C1-C4 alkyl and C1-C4 alkoxy; $R^4$ and $R^5$ are independently hydrogen, C1-C4 alkyl, C2-C4 alkenyl, C2-C4 alkynyl or a group I element such as Na; $R^{11}$ and $R^{12}$ are independently hydrogen or C1-C4 alkyl; and z is 1, 2, 3 or 4.

As used herein, a C1-C4 alkyl group or moiety can be linear or branched but is preferably linear. Suitable such alkyl groups and moieties include methyl, ethyl, n-propyl, i-propyl, n-butyl, sec-butyl and tert-butyl.

As used herein, a C2-C4 alkenyl group or moiety can be linear or branched but is preferably linear. It contains one or more carbon-carbon double bonds. It is preferably a C2-C3 alkenyl group. Suitable such alkenyl groups and moieties include vinyl, allyl, propenyl and butenyl, e.g. $CH_2C(Me)=CH_2$.

As used herein, a C2-C4 alkynyl group or moiety can be linear or branched but is preferably linear. It contains one or more carbon-carbon triple bonds. It is preferably a C2-C3 alkynyl group. Suitable alkynyl groups and moieties include ethynyl, propynyl, and butynyl, and isomers thereof.

As used herein, a C3-C6 cycloalkyl group is typically a C4, C5 or C6 cycloalkyl group, more preferably a C5 or C6 cycloalkyl group.

An alkyl, alkenyl, alkynyl or cycloalkyl group is unsubstituted.

As used herein and unless otherwise stated, a heterocyclyl group or moiety is a saturated 5- to 7-membered ring system in which the ring contains at least one heteroatom. Typically, the ring contains up to three heteroatoms, e.g. one or two heteroatoms, selected from O, S and N. Thus, a heterocyclyl group or moiety is typically a 5- to 7-membered ring containing one, two or three heteroatoms selected from O, S and N. Suitable such heterocyclyl groups and moieties include, for example, monocyclic saturated 5- to 7-membered rings, more preferably monocyclic saturated 5- to 6-membered rings such as tetrahydrofuranyl, piperidinyl, oxazolidinyl, morpholinyl, thiomorpholinyl, pyrrolidinyl, dioxolanyl, piperidonyl, piperazinyl, tetrahydropyranyl and 1,4-diazepanyl, more preferably pyrrolidinyl, piperazinyl, tetrahydropyranyl and piperidinyl.

A heterocyclyl group may be substituted or unsubstituted. Each ring atom may be unsubstituted or may carry one or two substituents. If desired, a nitrogen atom may be disubstituted and a sulphur atom may be substituted, providing a charged heteroatom. Typically, a heterocyclyl group carries up to three substituents, e.g. one or two substituents. The heterocycle may be connected to the remainder of the molecule by a bond to any of its available ring positions. Suitable substituents are C1-C4 alkyl and C1-C4 alkoxy, e.g. methyl, ethyl, methoxy and ethoxy, preferably methyl.

Preferably, $R^1$, $R^2$ and $R^3$ are independently hydrogen, C1-C4 alkyl, C2-C4 alkenyl, C2-C4 alkynyl, C3-C6 cycloalkyl, or an unsubstituted 5- to 6-membered heterocyclyl group. More preferably, $R^1$, $R^2$ and $R^3$ are independently hydrogen, C1-C4 alkyl, C3-C6 cycloalkyl, or an unsubstituted pyrrolidinyl, piperazinyl, tetrahydropyranyl or piperidinyl group.

Preferably, $R^4$ and $R^5$ are independently hydrogen, C1-C4 alkyl, or a group I element such as Na. More preferably, $R^4$ and $R^5$ are independently hydrogen, methyl, ethyl, or Na.

Preferably, $R^{11}$ and $R^{12}$ are hydrogen.

Preferably, z is 1 or 2. More preferably z is 1.

Preferably R is a group of formula $-O-CO-OR^1$, $-O-CO-R^1$, $-O-CO-NR^1R^2$, $-O-CO-(CH_2)_z-NR^1R^2$, $-OR^1$, $-O-(CR^{11}R^{12})_z-O-CO-R^3$ or $-O-P(O)(OR^4)(OR^5)$. More preferably, R is a group of formula $-O-COR^1$, $-O-CO-NR^1R^2$, $-O-CO-(CH_2)_z-NR^1R^2$, $-OR^1$, $-O-(CR^{11}R^{12})_z-O-CO-R^3$ or $-O-P(O)(OR^4)(OR^5)$.

In one embodiment, R is a group of formula $-O-CO-OR^1$, $-O-CO-R^1$, $-O-CO-NR^1R^2$, $-O-CO-(CH_2)_z-NR^1R^2$, $-OR^1$, $-O-(CR^{11}R^{12})_z-O-CO-R^3$ or $-O-P(O)(OR^4)(OR^5)$, wherein: $R^1$, $R^2$ and $R^3$ are independently hydrogen, C1-C4 alkyl, C2-C4 alkenyl, C2-C4 alkynyl, C3-C6 cycloalkyl, or an unsubstituted 5- to 6-membered heterocyclyl group; $R^4$ and $R^5$ are independently hydrogen, C1-C4 alkyl, or a group I element such as Na; and z is 1 or 2. More preferably R is a group of formula $-O-COR^1$, $-O-CO-NR^1R^2$, $-O-CO-(CH_2)_z-NR^1R^2$, $-OR^1$, $-O-(CR^{11}R^{12})_z-O-CO-R^3$ or $-O-P(O)(OR^4)(OR^5)$, wherein $R^1$, $R^2$ and $R^3$ are independently hydrogen, C1-C4 alkyl, C3-C6 cycloalkyl, or an unsubstituted pyrrolidinyl, piperazinyl, tetrahydropyranyl or piperidinyl group; $R^4$ and $R^5$ are independently hydrogen, methyl, ethyl, or Na; and z is 1.

R may, for example, be $-OP(O)(ONa)_2$, $-OP(O)(OH)_2$, $-OC(=O)CH_2N(H)CH_3$, $-OC(=O)C_4NH_8$, $-OC(=O)CH_3$, $-OC(=O)N(CH_3)_2$ or $-OCH_2OC(=O)C(CH_3)_3$.

2-(1,5-dimethyl-3-phenyl-1H-pyrrol-2-yl)-N-(4-(4-(5-fluoropyrimidin-2-yl)piperazin-1-yl)phenyl)-2-oxoacetamide may be delivered as a pharmaceutically acceptable salt of the prodrug.

Synthesis 2-(1,5-dimethyl-3-phenyl-1H-pyrrol-2-yl)-N-(4-(4-(5-fluoropyrimidin-2-yl)piperazin-1-yl)phenyl)-2-oxoacetamide may be synthesised by reacting a compound of formula (II) with a compound of formula (III). Typically the reaction takes place in the presence of an organic solvent and a base. Preferably the solvent is dichloromethane or tetrahydrofuran and the base is triethylamine or pyridine. Typically the reaction is carried out at 0° C. initially while the reagents are added and then stirred at room temperature until the reaction is complete. The compound of formula (III) is typically available from commercial sources or can be prepared by known methods.

(II)

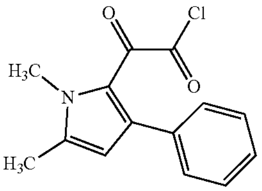

(III)

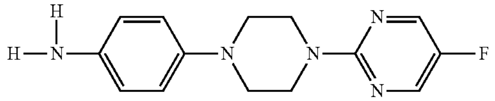

The compound of formula (II) may be prepared by reacting a compound of formula (IV) with, preferably, oxalyl chloride. Typically the reaction takes place in an organic solvent. Preferably, the solvent is dichloromethane. Typically, the reaction is carried out at 0° C. initially while the reagents are added and then stirred at room temperature until the reaction is complete.

(IV)

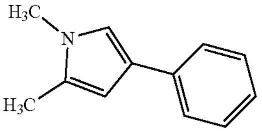

All of the starting materials referred to in the reactions described above are available from commercial sources or can be prepared by analogy with known methods.

Pharmaceutical Combination

The methods of the present invention may comprise administration to said subject of a pharmaceutical combination comprising: (i) 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof, and (ii) a second antifungal agent.

Typically, the pharmaceutical combination is a pharmaceutical combination in which compound (i) and the second antifungal agent (ii) are formulated for separate, simultaneous or successive administration. For simultaneous administration, (i) and (ii) may for example be provided in a single composition. For separate or successive administration, (i) and (ii) may, for example, be provided as a kit.

The second antifungal agent used in the invention can be any suitable antifungal agent that the skilled person would judge to be useful in the circumstances. Particularly suitable classes of antifungal agents include azoles, polyenes, purine nucleotide inhibitors, pyrimidine nucleotide inhibitors, mannan inhibitors, protein elongation factor inhibitors, chitin synthase inhibitors, Beta-glucan synthase inhibitors, echinocandins, allylamines, anti-HSP90 antibodies or inhibitors, bactericidal/permeability inducing protein products and polyoxins. Other suitable antifungal agents which do not fall within the classes above include the compounds 5-fluoro-1,3-dihydro-1-hydroxy-2,1-benzoxaborole (AN269), 5-chloro-1,3-dihydro-1-hydroxy-2,1-benzoxaborole (AN2718) and icofungipen. For instance, the second antifungal agent may be selected from the group consisting of azoles, polyenes, purine nucleotide inhibitors, pyrimidine nucleotide inhibitors, mannan inhibitors, protein elongation factor inhibitors, echinocandins, allylamines, anti-HSP90 antibodies, bactericidal/permeability inducing protein products or polyoxins, or one of the compounds 5-fluoro-1,3-dihydro-1-hydroxy-2,1-benzoxaborole (AN269), 5-chloro-1,3-dihydro-1-hydroxy-2,1-benzoxaborole (AN2718), icofungipen, VT116 or SCY078.

VT116 is 2-Pyridineethanol, α-(2,4-difluorophenyl)-β,β-difluoro-α-(1H-tetrazol-1-ylmethyl)-5-[4-(2,2,2-trifluoroethoxy)phenyl]-, (αR)-,

VT-1161

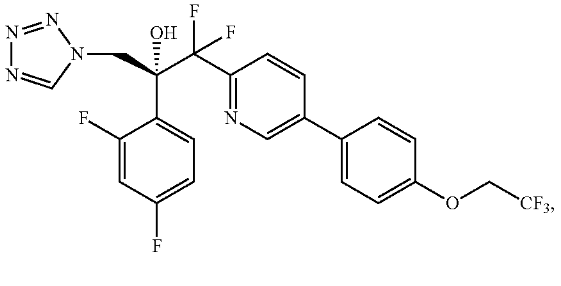

and SCY078 078 (aka MK-3118) is a semi-synthetic derivative of enfumafungin, 4H-1,4a-Propano-2H-phenanthro[1,2-c]pyran-7-carboxylic acid, 15-[(2R)-2-amino-2,3,3-trimethylbutoxy]-8-[(1R)-1,2-dimethylpropyl]-1,6,6a,7,8,9,10,10a,10b,11,12,12a-dodecahydro-1,6a,8,10a-tetramethyl-14-[5-(4-pyridinyl)-1H-1,2,4-triazol-1-yl]-, (1S,4aR,6aS,7R,8R,10aR,10bR,12aR,14R,15R):

SCY-078

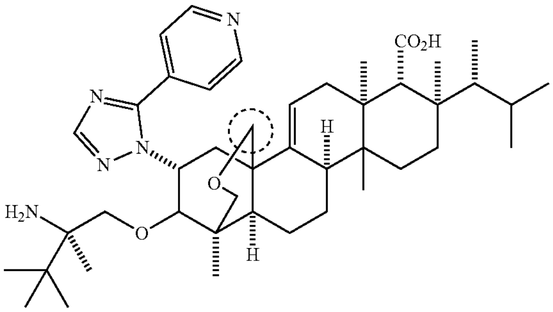

Preferred azoles are clotrimazole, econazole, bifonazole, butoconazole, fenticonazole, fluconazole, isoconazole, itraconazole, ketoconazole, miconazole, oxiconazole, sertaconazole, sulconazole, tioconazole, isavuconazole, ravuconazole, posaconazole, terconazole voriconazole, luliconazole and PC945. PC945 is a triazole antifungal, chemical name 4-[4-(4-{[(3R,5R)-5-(2,4-difluorophenyl)-5-(1H-1,2,4-triazol-1-ylmethypoxolan-3-yl]methoxy}-3-methylphenyl)piperazin-1-yl]-N-(4-fluorophenyl)benzamide.

Preferred echinocandins are anidulafungin, caspofungin micafungin and biafungin. Preferred allylamines are terbinafine, butenafine, amorolfine and naftifine. Preferred polyenes are amphotericin B and nystatin. A preferred example of a purine or pyrimidine nucleotide inhibitor is flucytosine. A preferred mannan inhibitor is pradamicin. A preferred protein elongation factor inhibitor is sordarin and analogues thereof. A preferred polyoxin is nikkomycin Z.

Other antifungal agents that may be the second antifungal agent include APX001a (3-(3-(4-(pyridine-2-yloxymethyl)-benzyl)-isoxazol-5-yl)-pyridin-2-ylamine) and APX001 (2-amino-1-((phosphonooxy) methyl)-3-(3-((4-((2-pyridinyloxy) methyl) phenyl) methyl)-5-isoxazolyl)-pyridinium).

Particularly preferred second antifungal agents are caspofungin, micafungin, anidulafungin, amphotericin B, voriconazole, posaconazole, isavuconazole, fluconazole and itraconazole. Further preferred antifungal agents are azoles selected from posaconazole, fluconazole, voriconazole, isavuconazole and combinations thereof.

In some embodiments, the second antifungal agent is an azole such as fluconazole.

The pharmaceutical combination may be formulated as a single composition. Thus, the pharmaceutical composition may, for example, comprise (i) 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, (ii) a second antifungal agent as defined herein, such as fluconazole, and (iii) a pharmaceutically acceptable carrier or diluent.

Administration

The compound 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may be administered in a variety of dosage forms.

Thus, it can be administered orally, for example as a tablet, troche, capsules, lozenge, aqueous or oily suspension, dispersible powder or granules.

The compound 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may also be administered parenterally, either subcutaneously, intravenously, intramuscularly, intrasternally, transdermally or by infusion techniques, for example, intravenous administration may be used.

Depending on the vehicle and concentration used, the drugs can either be suspended or dissolved in the vehicle. Advantageously, adjuvants such as a local anaesthetic, preservative and buffering agent can be dissolved in the vehicle.

2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may also be administered as suppositories or 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may be administered by inhalation in the form of an aerosol via an inhaler or nebuliser. Alternatively, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, may be administered topically, for example, as a cream, foam, gel, lotion, or ointment.

2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, and optionally a second antifungal agent, is typically formulated for administration with a pharmaceutically acceptable carrier or diluent. For example, solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be solutions, syrups, emulsions and suspensions. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may include pharmaceutically active compounds in which the average particle size has undergone particle size reduction by micronisation or nanonisation technologies. For instance, the average particle size of the compound of the invention may have undergone particle size reduction by micronisation or nanonisation technologies.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water and solubilising agents, e.g. cyclodextrins or modified cyclodextrins, or preferably they may be in the form of sterile, aqueous, isotonic saline solutions.

Nanoformulations are also envisaged.

For topical application to the skin, the compound may, for example, be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the compound may be formulated for aerosol delivery for example, by pressure-driven jet atomizers or ultrasonic atomizers, or preferably by propellant-driven metered aerosols or propellant-free administration of micronized powders, for example, inhalation capsules or other “dry powder” delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the compound may be made up into a solution or suspension in a suitable sterile aqueous or non aqueous vehicle. Additives, for instance buffers such as sodium metabisulphite or disodium edetate; preservatives including bactericidal and fungicidal agents such as phenyl mercuric acetate or nitrate, benzalkonium chloride or chlorhexidine, and thickening agents such as hypromellose may also be included.

In one embodiment, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered intravenously. If a second antifungal agent is administered separately, simultaneously or successively, the second antifungal agent may be administered intravenously or by a different mode of administration, which different mode of administration may be as defined herein.

The dosage form employed may depend upon a variety of factors including the severity of the infection and general overall health of the patient. Preferred routes of administration of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, include oral administration and intravenous administration.

When, for example, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof is part of a pharmaceutical combination as defined herein, formulated for separate, simultaneous or successive administration, (a) 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, and (b) the second antifungal agent may be administered by the same mode of administration or by different modes of administration.

Pharmaceutical Composition

The methods of the present invention may comprise administration to said subject of a pharmaceutical composition comprising an effective amount of 2-(1,5-dimethyl-3-phenyl-1H-pyrrol-2-yl)-N-(4-(4-(5-fluoropyrimidin-2-yl) piperazin-1-yl)phenyl)-2-oxoacetamide or a pharmaceutically acceptable salt thereof, together with one or more pharmaceutically acceptable carriers and/or excipients. Any suitable carriers and/or excipients may be used. Suitable excipients include, but are not limited to, hydroxypropyl methyl cellulose acetate succinate (HPMC-AS) and cyclodextrin or modified cyclodextrin. The cyclodextrin or modified cyclodextrin may, for example, be hydroxy propyl beta cyclodextrin (HPBC). The carrier may, for example, be sterile water, or may be in the form of a sterile, aqueous, isotonic saline solution.

In one embodiment, the mass ratio of the compound of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, to excipient is from 1:100 to 1:1, preferably wherein the mass ratio of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, to excipient is from 1:15 to 1:2.

The pharmaceutical composition typically contains up to 85 wt % of 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof. More typically, it contains up to 50 wt %, e.g., up to 30 wt %, of 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof. In one embodiment, the pharmaceutical composition typically contains about 20 wt % of 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof. Preferred pharmaceutical compositions are sterile and pyrogen free.

The pharmaceutical composition may, for example, comprise spray-dried particles of 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof. The spray-dried particles may, for example, be obtainable by spray-drying from a solution comprising an organic solvent selected from ethanol or ethanol and water.

When, for example, the pharmaceutical composition is composition suitable for parenteral administration, said pharmaceutical composition may comprise pray-dried particles of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, at a concentration of from 1 mg/mL to 10 mg/mL. The excipient may, for example, be clodextrin or modified cyclodextrin, e.g., hydroxy propyl beta cyclodextrin. The spray-dried particles may, for example, be obtainable by spray-drying from a solution comprising an organic solvent selected from ethanol or ethanol and water.

Effective Amount

A therapeutically effective amount of 2-(1,5-dimethyl-3-phenyl-1H-pyrrol-2-yl)-N-(4-(4-(5-fluoropyrimidin-2-yl) piperazin-1-yl)phenyl)-2-oxoacetamide, or a pharmaceutically acceptable salt thereof may be administered to a patient.

Typically, in the methods of the invention, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject more than once a day, for example, at least two, three, four or five times daily. Preferably, 2-(1,5-dimethyl-3-phenyl-1H-pyrrol-2-yl)-N-(4-(4-(5-fluoropyrimidin-2-yl) piperazin-1-yl)phenyl)-2-oxoacetamide, or a pharmaceutically acceptable salt thereof, is administered to said subject at least two, three or four times daily.

In one embodiment, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject a least twice daily, e.g., twice daily.

In one embodiment, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject at least three times daily, e.g, three or four times daily, preferably three times daily.

As person skilled in the art will appreciate, the total daily dose will depend upon the age, weight and conditions of the subject to be treated, the type and severity of the disease and the frequency and route of administration. The daily dose may also change when 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof is used in combination with a further antifungal agent (or further antifungal agents).

The second antifungal agent is typically administered at or below the standard dose used for that drug. An advantage of the use of combinations is that known antifungal agents may be administered in lower doses than are currently used, resulting in a reduction in toxic effects. 2-(1,5-dimethyl-3-phenyl-1H-pyrrol-2-yl)-N-(4-(4-(5-fluoropyrimidin-2-yl) piperazin-1-yl)phenyl)-2-oxoacetamide, or a pharmaceutically acceptable salt thereof, is typically administered to the patient in a non-toxic amount.

A typical daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is from 1 to 200 mg/kg of body weight, e.g., from 2 to 100 mg/kg or from 2 to 10 mg/kg of body weight.

In one embodiment, the total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject is 2 to 50 mg/kg of body weight, e.g., 20 to 50 mg/kg of body weight. The maximum total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject may, for example, be about 40 mg/kg of body weight, about 20 mg/kg/d of body weight or about 2 mg/kg/d of body weight In some embodiments, 2-(1,5-dimethyl-3-phenyl-1H-pyrrol-2-yl)-N-(4-(4-(5-fluoropyrimidin-2-yl)piperazin-1-yl) phenyl)-2-oxoacetamide, or a pharmaceutically acceptable salt thereof, is administered to said subject three times daily and the total daily dose of 2-(1,5-dimethyl-3-phenyl-1H-pyrrol-2-yl)-N-(4-(4-(5-fluoropyrimidin-2-yl)piperazin-1- yl)phenyl)-2-oxoacetamide, or a pharmaceutically acceptable salt thereof, administered to the subject is 0.5 to 50 mg/kg of body weight.

EXEMPLARY EMBODIMENTS

Embodiment 1. Method of treating or preventing a fungal infection in a subject, wherein the infection is caused by a *Coccidioides* species, which method comprises:
administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof,
wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject at least twice daily.

Embodiment 2. The method according to embodiment 1, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject at least three times daily Embodiment 3. The method according to embodiment 1 or embodiment 2, which method comprises administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide.

Embodiment 4. The method according to any one of embodiments 1 to 3, wherein a total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject is from 2 to 50 mg/kg.

Embodiment 5. The method according to any one of embodiments 1 to 4, wherein the *Coccidioides* species is *Coccidioides immitis* and/or *Coccidioides posadasii.*

Embodiment 6. The method according to any one of embodiments 1 to 5, wherein the subject is suffering from or susceptible to coccidioidomycosis.

Embodiment 7. The method according to embodiment 6, wherein the coccidioidomycosis is disseminated coccidioidomycosis.

Embodiment 8. The method according to any one of embodiments 1 to 7, wherein the 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject orally.

Embodiment 9. The method according to any one of embodiments 1 to 8, wherein the subject's fungal burden remains suppressed after cessation of treatment.

Embodiment 10. The method according to any one of embodiments 1 to 9, wherein the fungal burden is the fungal burden in the subject's blood plasma, brain tissue or lung tissue.

Embodiment 11. The method according to any one of embodiments 1 to 10, wherein the fungal burden is suppressed for at least 7 days after cessation of treatment.

Embodiment 12. The method according to any one of embodiments 1 to 11, which method comprises administration to said subject of a pharmaceutical composition comprising an effective amount of 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof, together with one or more pharmaceutically acceptable carriers and/or excipients.

Embodiment 13. The method according to any one of embodiments 1 to 12, which method comprises administration to said subject of a pharmaceutical combination comprising: (i) 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof, and (ii) a second antifungal agent.

Embodiment 14. The method according to embodiment 13, wherein the second antifungal agent is fluconazole.

Embodiment 15. Method of treating or preventing a fungal infection in a subject, wherein the infection is caused by a *Coccidioides* species, which method comprises:
administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof,
wherein pyrimidine starvation in *Coccidioides* cells in said subject is maintained for the duration of treatment.

Embodiment 16. The method according to embodiment 15, which method comprises administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide.

Embodiment 17. The method according to embodiment 15 or embodiment 16, wherein the Cmin levels of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, in the subject's blood plasma are maintained at or above the level required to maintain pyrimidine starvation in *Coccidioides* cells for the duration of treatment.

Embodiment 18. The method according to any one of embodiments 15 to 17, wherein Cmin in said subject's blood plasma is maintained at between 3 and 500 ng/ml.

Embodiment 19. The method according to any one of embodiments 15 to 18, wherein the subject's fungal burden remains suppressed after cessation of treatment.

Embodiment 20. The method according to any one of embodiments 15 to 19, wherein the fungal burden is the fungal burden in the subject's blood plasma, brain tissue or lung tissue.

Embodiment 21. The method according to any one of embodiments 15 to 20, wherein the duration of treatment is at least one day.

Embodiment 22. The method according to any one of embodiments 15 to 21, wherein the fungal burden is suppressed for at least 7 days after cessation of treatment.

Embodiment 23. The method according to any one of embodiments 15 to 22, wherein the *Coccidioides* species is *Coccidioides immitis* and/or *Coccidioides posadasii.*

Embodiment 24. The method according to any one of embodiments 15 to 23, wherein the subject is suffering from or susceptible to coccidioidomycosis.

Embodiment 25. The method according to embodiment 24, wherein the coccidioidomycosis is disseminated coccidioidomycosis.

Embodiment 26. The method according to any one of embodiments 15 to 25, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject twice daily.

Embodiment 27. The method according to any one of embodiments 15 to 25, wherein 2-(1,5-dimethyl-3-phenyl-1H-pyrrol-2-yl)-N-(4-(4-(5-fluoropyrimidin-2-yl)

piperazin-1-yl)phenyl)-2-oxoacetamide, or a pharmaceutically acceptable salt thereof, is administered to said subject three times daily.

Embodiment 28. The method according to any one of embodiments 15 to 27, wherein a total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject is from 2 to 50 mg/kg.

Embodiment 29. Method of treating or preventing a fungal infection in a subject, wherein the infection is caused by a *Coccidioides* species, which method comprises:

administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, wherein the subject's fungal burden remains suppressed after cessation of treatment.

Embodiment 30. The method according to embodiment 29, which method comprises administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide.

Embodiment 31. The method according to embodiment 29 or embodiment 30, wherein the fungal burden is the fungal burden in the subject's blood plasma, brain tissue or lung tissue.

Embodiment 32. The method according to any one of embodiments 29 to 31, wherein the fungal burden is suppressed for at least 7 days after cessation of treatment.

Embodiment 33. The method according to any one of embodiments 29 to 32, wherein the *Coccidioides* species is *Coccidioides immitis* and/or *Coccidioides posadasii*.

Embodiment 34. The method according to any one of embodiments 29 to 33, wherein the subject is suffering from or susceptible to coccidioidomycosis.

Embodiment 35. The method according to embodiment 34, wherein the coccidioidomycosis is disseminated coccidioidomycosis.

Embodiment 36. The method according to any one of embodiments 29 to 35, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject twice daily.

Embodiment 37. The method according to any one of embodiments 29 to 36, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject three times daily.

Embodiment 38. The method according to any one of embodiments 29 to 37, wherein a total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject is from 2 to 50 mg/kg.

Embodiment 39. Method of treating or preventing disseminated coccidioidomycosis, which method comprises:

administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof.

Embodiment 40. The method according to embodiment 39, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject twice daily.

Embodiment 41. The method according to embodiment 39, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject three times daily.

Embodiment 42. The method according to any one of embodiments 39 to 41, which method comprises administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide.

Embodiment 43. The method according to any one of embodiments 39 to 42, wherein a total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject is from 2 to 50 mg/kg.

The following examples illustrate the invention but are not intended to limit the scope of the invention.

Examples

1. Synthesis of 2-(1,5-dimethyl-3-phenyl-1H-pyrrol-2-yl)-N-(4-(4-(5-fluoropyrimidin-2-yl)piperazin-1-yl)phenyl)-2-oxoacetamide The synthetic scheme below provides a method of synthesis of:

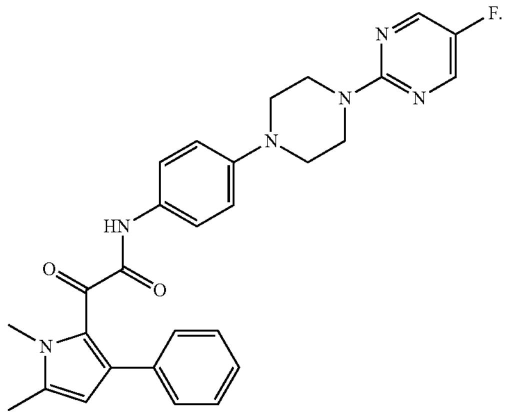

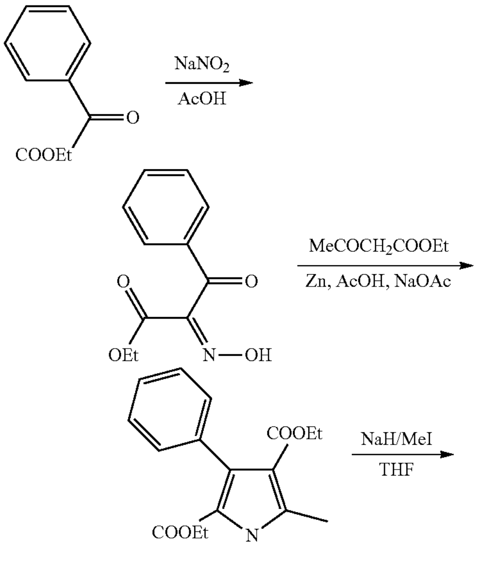

-continued

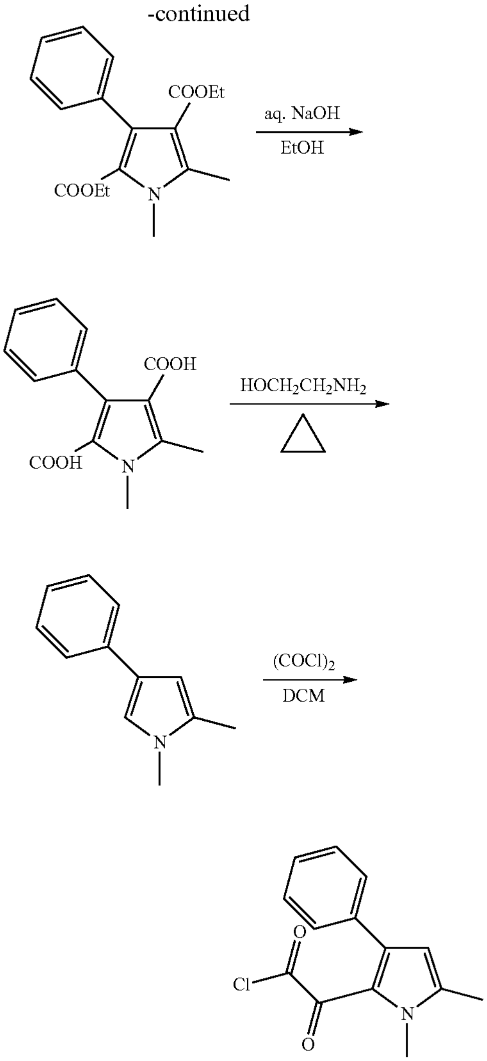

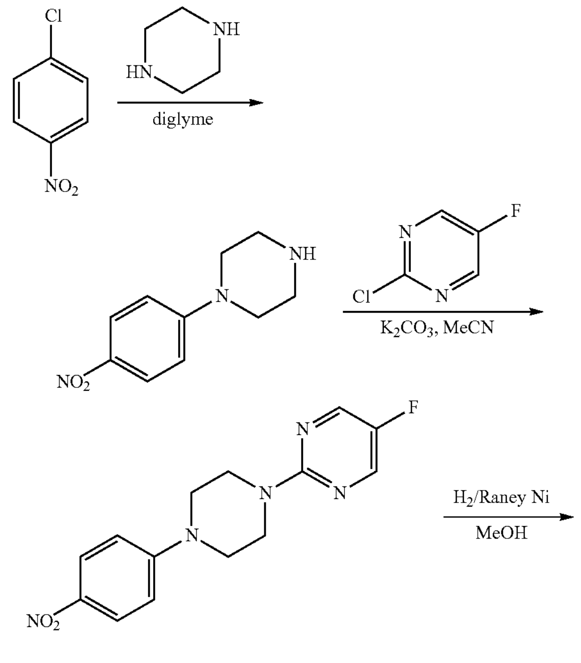

-continued

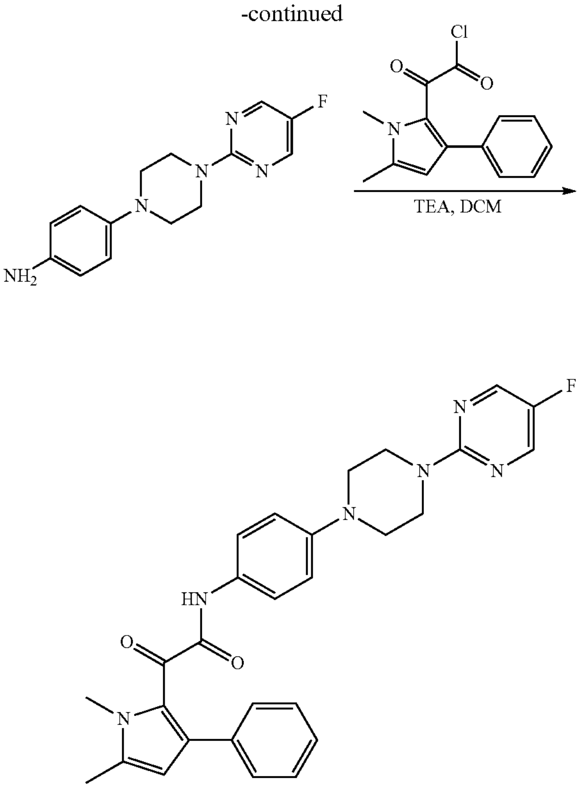

2-Hydroxyimino-3-oxo-3-phenyl Propionic Acid Ethyl Ester (A)

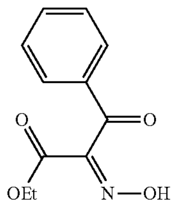 [SMILES: CCOC(=O)/C(=N/O)C(=O)c1ccccc1]

A solution of sodium nitrite (1.07 Kg, 45.62 mol) in water (4 L) was added slowly to a solution of ethyl benzoyl acetate (2 Kg, 10.41 mol) in glacial acetic acid (6 L), at 0-10° C. over a period of 2 h. The reaction mass was warmed to room temperature and stirred for a further 1 h. Water (2.5 L) was added and the mixture stirred for a further 1 h. Filtered under suction, washed with water (2 L). The solid was dissolved in chloroform (8 L) and washed with water (2×500 mL), brine solution (2×500 mL), dried over anhydrous sodium sulfate and concentrated in vacuo to dryness to afford 2.0 Kg (86%) of 2-hydroxyimino-3-oxo-3-phenyl propionic acid ethyl ester A as a white solid. [TLC system: Ethyl acetate:Pet ether (3:7); $R_f$ value: 0.28].

5-Methyl-3-phenyl-1H-pyrrole-2,4 Dicarboxylic Acid Diethyl Ester (B)

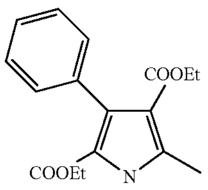 [SMILES: CCOC(=O)c1[nH]c(C)c(C(=O)OCC)c1-c1ccccc1]

A mixture of ethyl acetoacetate (329 g, 2.53 mol), zinc dust (443 g, 6.78 mol) and anhydrous sodium acetate (463 g, 5.65 mol) in glacial acetic acid (800 mL) were heated to 60° C. A solution of A (500 g, 2.26 mol) in glacial acetic acid (1.5 L) was added in three portions under vigorous stirring over a period of ~1 h. The reaction mixture was maintained at 60-75° C. for 3 h. Additional zinc dust (221 g, 3.39 mol) was added to the reaction mass over 15 min and the mixture was stirred at 60-75° C. for 1 h, cooled to room temperature and filtered the solids. The filtrate was evaporated in vacuo and the residue was co-distilled with toluene (2×500 mL). Water (5 L) and ethyl acetate (1 L) were added to the residue and stirred till two clear layers were obtained. The organic layer washed successively with water (2×500 mL), saturated bicarbonate solution (2×500 mL), brine (2×500 mL) dried over anhydrous sodium sulfate and concentrated to give 360 g of crude gummy product. This was stirred with a mixture of dichloromethane in pet ether (200 mL: 1200 mL; 1:6) at room temperature for 15 min, filtered and washed with pet ether (100 mL) to afford 250 g (36%) of 5-methyl-3-phenyl-1H-pyrrole-2,4 dicarboxylic acid diethyl ester B as off-white solid. [TLC system: ethyl acetate:Pet ether (3:7); $R_f$ value: 0.45]. Similarly 1.5 Kg (500 g×3) of A was converted to 500 g [245 g (36%)+255 g (37%)+250 g (36%)] of B in three batches.

1,5-Dimethyl-3-phenyl-1H-pyrrole-2,4-dicarboxylic Acid Diethyl Ester (C)

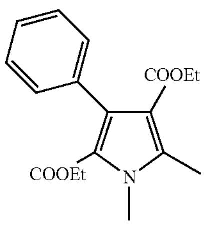 [SMILES: CCOC(=O)c1c(-c2ccccc2)c(C(=O)OCC)n(C)c1C]

A solution of B (1 Kg, 3.322 mol) in dry tetrahydrofuran (4 L) was added to slurry of sodium hydride (60% w/w; 254 g, 6.644 mol) in dry tetrahydrofuran (4 L) at 0° C. over 1 h. The reaction mass was warmed to room temperature and stirred for 1 h and again cooled to 0° C. Methyl iodide (517 mL; 8.305 mol) was added over ½ h and the reaction mixture stirred at room temperature for 18 h. The reaction mixture was quenched with ice-water (100 mL) and 1N hydrochloric acid (2 L) was added. The organic layer was separated and the aqueous layer was extracted with dichloromethane (2×500 mL). The combined organic layers were washed successively with brine (2×200 mL), dried over anhydrous sodium sulfate and concentrated to dryness to afford 950 g (91%) of 1,5-dimethyl-3-phenyl-1H-pyrrole-2,4-dicarboxylic acid diethyl ester C as a yellow solid [TLC system: ethyl acetate:Pet ether (3:7); $R_f$ value: 0.56].

1,5-Dimethyl-3-phenyl-1H-pyrrole-2,4-dicarboxylic Acid (D)

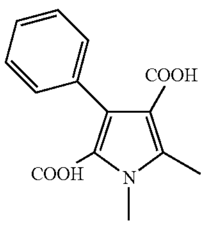 [SMILES: Cc1c(C(=O)O)c(-c2ccccc2)c(C(=O)O)n1C]

A solution of sodium hydroxide (1.21 Kg, 30.25 mol) in water (3.6 L) was added to a solution of C (950 g, 3.025 mol) in ethanol (5 L) and heated at reflux for 15 h. Ethanol was evaporated under reduced pressure, the residue was diluted with water (1 L) and chilled to 0° C. Concentrated hydrochloric acid (2 L) was slowly added to adjust pH to ~2, while maintaining temperature below 10° C. and stirred for 1 h. The precipitated solid was filtered, washed with water (1 L) and pet ether (1 L) and dried under vacuum at 60° C., to afford 550 g (70%) of 1,5-Dimethyl-3-phenyl-1H-pyrrole-2,4-dicarboxylic acid D as a white solid. [TLC system: ethyl acetate:Pet ether (3:7); $R_f$ value: 0.15].

1,2-Dimethyl-4-phenyl-1H-pyrrole (E)

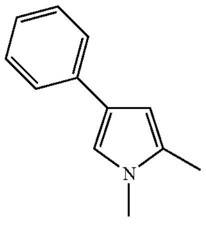

A suspension of E (550 g, 2.123 mol) in ethanolamine (1.5 L) was heated to 175° C. (under $N_2$) and maintained for 1 h. The reaction mixture was cooled to room temperature, diluted with water (500 mL) and extracted with ethyl acetate (3×200 mL). The combined organic layers were washed successively with water (2×100 mL) and brine (2×100 mL), dried over anhydrous sodium sulfate and concentrated in vacuo below 40° C. to give a crude product. Flash chromatography over neutral alumina using 5% ethyl acetate in pet ether as eluent afforded 280 g (77%) of 1,2-dimethyl-4-phenyl-1H-pyrrole E, as a white solid. [TLC system: ethyl acetate:Pet ether (3:7); $R_f$ value: 0.75].

(1,5-Dimethyl-3-phenyl-1H-pyrrol-2-yl)-oxo-acetyl Chloride (F)

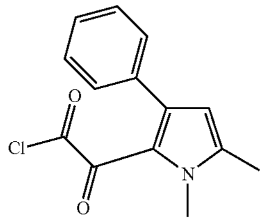 [SMILES: Cc1cc(-c2ccccc2)c(C(=O)C(=O)Cl)n1C]

Oxalyl chloride (116 mL, 1.286 mol) was added slowly to a cooled solution of E (250 g, 1.169 mol) in dry dichloromethane (3×200 mL) at 0° C. The reaction mixture was warmed to room temperature and stirred for 1 h. The solvent was evaporated to dryness in vacuo to afford 340 g (89%) of 1,5-dimethyl-3-phenyl-1H-pyrrol-2-yl)-oxo-acetyl chloride F as a brown oily liquid. [TLC system: ethyl acetate:Pet ether (3:7); $R_f$ value: 0.65]

4-Nitro Phenyl Piperazine (G)

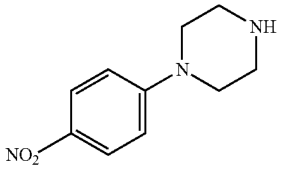 [SMILES: O=[N+]([O-])c1ccc(N2CCNCC2)cc1]

A solution of 1-chloro-4-nitro benzene (650 g, 4.140 mol) in diglyme (1 L) was added to a solution of piperazine (2.84 Kg, 33.12 mol) in diglyme (500 mL) at 100° C. and the resultant mass was stirred at 100° C. for 6 h. The mixture was cooled to 40-45° C., water (5 L) was added; warmed to room temperature and stirred for 1 h. The precipitated solid was filtered, washed with water (1 L), pet ether (500 mL) and dried to give 700 g (81%) of 4-nitro phenyl piperazine G as yellow colour solid. [TLC system: Ethyl acetate:pet ether (3:7); $R_f$ value: 0.70].

5-Fluoro-2-[4-(4-nitro-phenyl)-piperazin-1-yl]-pyrimidine (H)

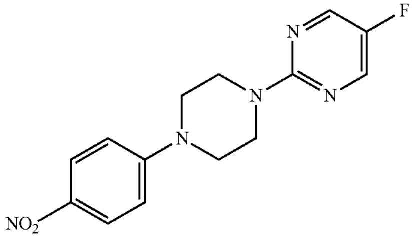 [SMILES: O=[N+]([O-])c1ccc(N2CCN(c3ncc(F)cn3)CC2)cc1]

2-Chloro-5-fluoropyrimidine (281 g, 2.12 mol) was added to suspension of 4-nitro phenyl piperazine G (400 g, 1.93 mol) and potassium carbonate (532 g, 3.85 mol) in diglyme (2.5 L), the resulting mixture was stirred at 100° C. for 6 h. On completion the mixture was cooled to 0° C. and filtered, the solid was taken in water (5 L) and stirred for 30 mins. The suspension was filtered, the solid cake was washed with water (1 L), pet ether (1 L) and dried under vacuum to afford 500 g (85%) of 5-fluoro-2-[4-(4-nitro-phenyl)-piperazin-1-yl]-pyrimidine H as yellow colour solid. [TLC system: Ethyl acetate:pet ether (3:7); $R_f$ value: 0.70].

4-[4-(5-Fluoro-pyrimidin-2-yl)-piperazin-1-yl]-phenyl Amine (I)

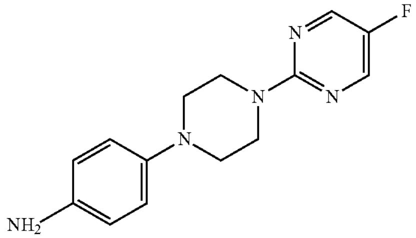

A solution of sodium dithionite (1.27 Kg, 7.32 mol) in water (6 L) was added to a suspension of H (500 g, 1.83 mol) and sodium bicarbonate (614 g, 7.32 mol) in methanol (6 L) at 65° C. The resultant mixture was stirred at 65° C. for 2 h. The reaction mass was cooled to 10-15° C. and filtered. The residue was partitioned between water (2 L) and ethyl acetate (5 L), the organic layer was washed with water (2 L), brine (2 L) and dried over anhydrous sodium sulfate. Concentrated in vacuo to afford 290 g (64%) of 4-[4-(5-fluoro-pyrimidin-2-yl)-piperazin-1-yl]-phenyl amine I as solid. [TLC system: Methanol:Chloroform (1:9); $R_f$ value: 0.50].

2-(1,5-Dimethyl-3-phenyl-1H-pyrrol-2-yl)-N-{4-[4-(5-fluoro-pyrimidin-2-yl)-piperazin-1-yl]-phenyl}-2-oxo-acetamide

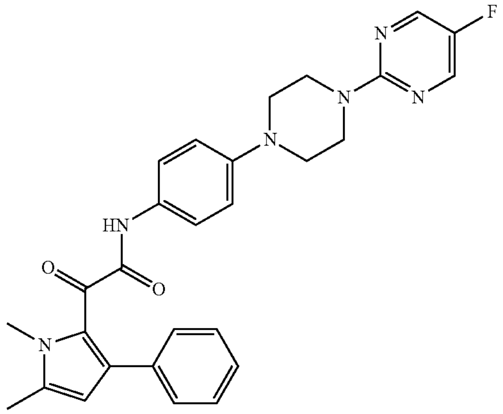 [SMILES: Cc1cc(-c2ccccc2)c(C(=O)C(=O)Nc2ccc(N3CCN(c4ncc(F)cn4)CC3)cc2)n1C]

A solution of F (332 g, 1.27 mol) in dichloromethane (3 L) was added to a stirred solution of I (290 g, 1.06 mol) and triethylamine (294 mL, 2.12 mol) in dichloromethane (3 L) at 0° C. The reaction mixture was warmed to room temperature and stirred for 30 min. The reaction mixture was quenched with water and extracted with dichloromethane (6×500 mL). The combined organic layers were washed successively with saturated sodium bicarbonate solution (1.5 L), water (1 L), brine (1.5 L) and finally dried over anhydrous sodium sulfate. The organic layer was stirred with neutral alumina (1 Kg) at room temperature for 30 min and filtered. The filtrate was concentrated in vacuo to give the crude compound which on washing with diethyl ether (300 mL) and followed by trituration with ethanol (3 L) at 80° C. for 1 h and cooled to room temperature, filtered, washed with ethanol (500 mL) followed by hexane (200 mL) and dried to give 340 g (64%) of 2-(1,5-dimethyl-3-phenyl-1H-pyrrol-2-yl)-N-{4-[4-(5-fluoro-pyrimidin-2-yl-piperazin-1-yl]-phenyl}-2-oxo-acetamide as yellow color solid. [TLC System: Ethyl acetate:Pet ether (1:1); $R_f$ value: 0.65].

NMR data for 2-(1,5-Dimethyl-3-phenyl-1H-pyrrol-2-yl)-N-{4-[4-(5-fluoro-pyrimidin-2-yl)-piperazin-1-yl]-phenyl}-2-oxo-acetamide NMR (400 MHz, $CDCl_3$)) are provided in FIG. 1. The signal was detected in the MS spectrum at 499.1 $[M+H]^+$.

2. Biological Activity

Materials and Methods

Isolates

For in vitro susceptibility testing, 59 clinical isolates of *Coccidioides* species were used. For the murine model, a clinical isolate of *C. immitis* (isolate UTHSCSA DI17-143) collected from a CNS shunt and sent to the University of Texas Health Science Center at San Antonio Fungus Testing Laboratory for clinical testing was used. For in vitro and in vivo studies, the isolates were grown on potato flake agar and potato dextrose agar (PDA), respectively, and arthroconidia were collected with the addition of sterile phosphate-buffered saline (PBS) and gentle scraping of the agar surface. For in vivo studies, the dislodged arthroconidium-PBS suspension was centrifuged and the supernatant was discarded. The arthroconidia were resuspended in PBS and filtered to remove hyphal fragments, and the number of arthroconidia was then adjusted to achieve the desired inoculum. Aliquots of the suspension were then plated onto PDA plates, and CFU were enumerated to determine the viability of the arthroconidia. These manipulations of the *Coccidioides* colonies and arthroconidia were conducted in a biosafety level 3 facility.

Antifungal Agents

For in vitro testing, olorofim powder was provided by F2G, Ltd. (Manchester, UK). Voriconazole powder for in vitro susceptibility testing was acquired from Sigma-Aldrich (St. Louis, Mo.). Stocks solutions of olorofim and voriconazole were prepared in dimethyl sulfoxide (DMSO), with further dilutions in RPMI 1640 medium (0.165 M morpholinepropanesulfonic acid [MOPS] [pH 7.0], with L-glutamine and without bicarbonate). For in vivo studies, olorofim was provided as a spray-dried dispersion, of which the active pharmaceutical ingredient constituted 20% (wt/wt) and the remainder was composed of the excipient hydroxypropyl methyl cellulose acetate succinate (HPMCAS). For dosing, the spray-dried dispersion of olorofim was suspended in PBS. A commercially available, pharmaceutical-grade formulation of fluconazole for intravenous dosing was purchased from a local pharmacy and was used as the positive control in in vivo studies.

In Vitro Susceptibility

The in vitro activities of olorofim and voriconazole were determined by broth macrodilution, according to Clinical and Laboratory Standards Institute guidelines (Clinical and Laboratory Standards institute. 2008. Reference method for broth dilution antifungal susceptibility testing of filamentous fungi; approved standard—2nd ed. Document M38-A2. Clinical and Laboratory Standards Institute, Wayne, Pa.). Fifty-nine clinical isolates were used, including 21 confirmed at the species level to be *C. immitis* and 24 to be *C. posaciasii* (Tintelnot K et al, 2007. Taxonomic and diagnostic markers for identification of *Coccidioides immitis* and *Coccidioides posadasii*. Med Mycol 45:385-393). The other 14 isolates were confirmed to be *Coccidioides* spp. through the use of a chemiluminescent DNA probe (AccuProbe *Coccidioides*; Hologic, San Diego, Calif.). Arthroconidia (final concentration, $0.5\times10^4$ to $2.5\times10^4$ arthroconidia/ml) were added to tubes containing serial 2-fold dilutions of olorofim (0.008 to 4 μg/ml) or voriconazole (0.03 to 16 μg/ml) in RIPMI 1640 medium, followed by incubation at 35° C. for at least 48 h. The MICs were recorded as the lowest concentrations that resulted in >80% inhibition of growth, compared to the drug-free control.

Murine Model of CNS Coccidioldomycosis

Four-week-old male ICR mice (n=10 mice per group; Envigo, Indianapolis, Ind.) were used, and they had access to food and water ad libitum. Mice were infected using previously described methods (Wiederhold N P et al, 2018. The novel fungal Cyp51 inhibitor VT-1598 is efficacious in experimental models of central nervous system coccidioidomycosis caused by *Coccidioides posadasii* and *Coccidioides immitis*. Antimicrob Agents Chemother 62:e02258-17). Briefly, anesthetized mice received intracranial inoculation with *C. immitis* arthroconidia (125 to 149 arthroconidia/mouse). Following inoculation, mice were monitored at least twice daily to prevent and to minimize unnecessary pain and distress; any animal that appeared moribund prior to the scheduled endpoint was euthanized. Both fungal burden and survival experiments were conducted, and 10 mice were included in each treatment group in each study. Treatment began 48 h after inoculation and continued for 7 days in the fungal burden arm and for 14 days in the survival arm. Mice were administered (by oral gavage) vehicle control (PBS) or olorofim at total daily doses of 20 mg/kg (either as 10 mg/kg twice daily or as 6.67 mg three times daily) or 40 mg/kg (either as 20 mg/kg twice daily or as 13.3 mg/kg three times daily). Fluconazole served as the positive control and was administered orally at 25 ng/kg twice daily. All mice were housed and utilized according to PHS guidelines, under an approved institutional animal care and use protocol.

Fungal Burden and Survival

In the survival arm, mice were monitored until day 30 postinoculation. Any animal that appeared moribund, according to prespecified conditions, was humanely euthanized, and death was recorded as occurring the next day. Brain fungal burdens were measured at the time of euthanasia, which occurred 1 day after the last dose of antifungal agent in the fungal burden arm and at the time of morbidity or at the predefined study endpoint (day 30 postinoculation) in the survival arm. Following collection, brains were weighed and then homogenized in sterile saline. The homogenates were diluted, and aliquots were plated onto PDA plates. After 72 to 96 h of incubation at 37° C., the number of CFU was counted and the fungal burden (CFU per gram of tissue) was determined.

Data Analysis

Differences in GM (geometric mean) ICs, which were calculated following $\log_2$ transformation of individual MIC values for olorofim and voriconazole, were assessed for significance by paired t test. Survival times were plotted for Kaplan-Meier analysis, and differences in median survival times and percentages of mice surviving were analyzed by the log-rank test and Fisher's exact test, respectively. Differences in brain fungal burdens were assessed by analysis of variance (ANOVA), with Tukey's post hoc test for multiple comparisons. P values of ≤0.05 were considered statistically significant.

PK Study

As part of a work up prior to performing a murine coccidiodes efficacy model in conjunction with the NIH and the San Antonio Fungal Laboratory, a PK study was carried out to determine the levels of F901318 in plasma, lung and brain of uninfected mice after oral doing at several doses.

The PK study was carried out on male and female mice dosed with 3 different dosing regimens of F901318. The regimes used were 10 mg/kg, 20 mg/kg and 30 mg/kg BD, of F901318 dosed orally as a spray dried dispersion in phosphate buffer. Samples were taken at several timepoints following the thirteenth dose (on the seventh day). Three animals of each sex were used for each timepoint.

Samples were frozen and shipped to Cyprotex, Macclesfield, UK on dry ice, where they were thawed and analysed for F901318 content by HPLC LC/MS. The level of F901318 measured in each sample were then provided to F2G for PK analysis.

Results

Summary PK Data

Summary PK data is provided below.

| | Plasma Females | | | Plasma males | | |
|---|---|---|---|---|---|---|
| | 10 mg/kg | 20 mg/kg | 30 mg/kg | 10 mg/kg | 20 mg/kg | 30 mg/kg |
| AUC 0-12 (ng · hr/ml) | 11421 | 26634 | 30836 | 8705 | 22121 | 27702 |
| Cmax (ng/ml) | 2113 | 4607 | 4110 | 2647 | 3907 | 4113 |
| Cmin (ng/ml) | 234 | 856 | 1083 | 204 | 746 | 696 |
| Tmax (hrs) | 1 | 0.5 | 1 | 0.5 | 1 | 1 |

| | Brain Females | | | Brain males | | |
|---|---|---|---|---|---|---|
| | 10 mg/kg | 20 mg/kg | 30 mg/kg | 10 mg/kg | 20 mg/kg | 30 mg/kg |
| AUC 0-12 (ng · hr/ml) | 6179 | 24152 | 25657 | 6347 | 16897 | 25553 |
| Cmax (ng/ml) | 958 | 3200 | 3193 | 1430 | 3363 | 3390 |
| Cmin (ng/ml) | 125 | 414 | 1041 | 639 | 471 | 592 |
| Tmax (hrs) | 0.5 | 0.5 | 1 | 0.5 | 1 | 0.5 |

| | Lung Females | | | Lung males | | |
|---|---|---|---|---|---|---|
| | 10 mg/kg | 20 mg/kg | 30 mg/kg | 10 mg/kg | 20 mg/kg | 30 mg/kg |
| AUC 0-12 (ng · hr/ml) | 9240 | 29634 | 36640 | 10517 | 24753 | 34664 |
| Cmax (ng/ml) | 2350 | 4490 | 5860 | 3136 | 4580 | 4780 |
| Cmin (ng/ml) | 250 | 821 | 1341 | 271 | 867 | 804 |
| Tmax (hrs) | 0.5 | 2.5 | 0.5 | 0.5 | 1 | 1 |

Figure 2:
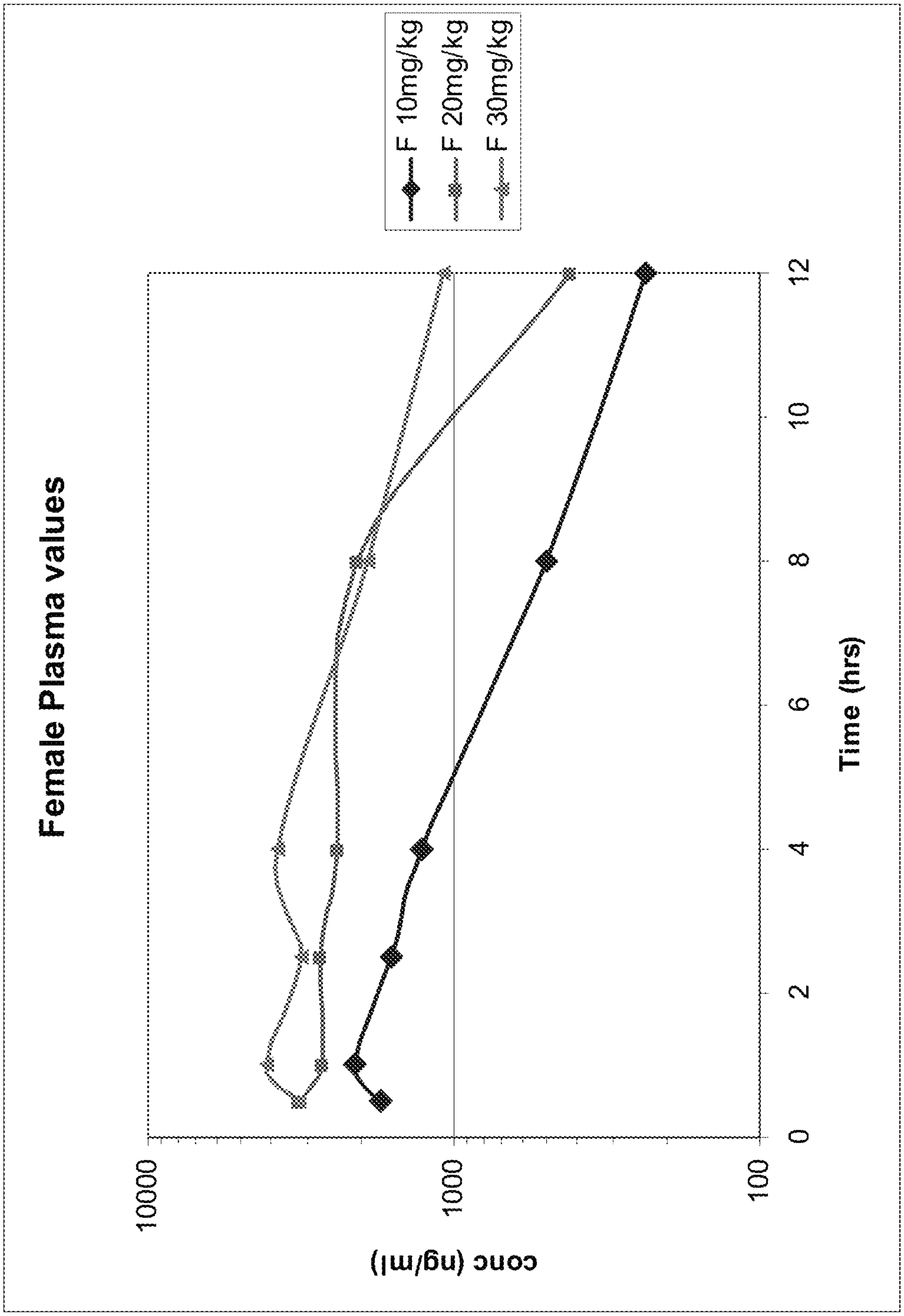
FIG. 2 provides information on the change in plasma levels with time for doses of 10 mg/kg, 20 mg/kg and 30 mg/kg olorofim BD.

FIG. 2 provides information on the change in plasma levels with time for doses of 10 mg/kg, 20 mg/kg and 30 mg/kg olorofim BD.

The following conclusions can be drawn from the data.

1) The Plasma Tmax occurs rapidly within 1 hour of dosing. Similar early Tmax values are seen in lung and brain tissue.
2) In most cases exposure is slightly higher in females compared with males.
3) Good drug levels are observed in lung and brain. Levels in brain are slightly lower than those in plasma whilst levels in lung are slightly higher.

In Vitro Susceptibility

MICs were measured, after 48 to 72 h of incubation at 35° C., as the lowest concentration that resulted in 80% inhibition of growth, compared to the growth control. $MIC_{50}$, MIC at which 50% of isolates were inhibited; $MIC_{90}$, MIC at which 90% of isolates were inhibited GM, geometric mean.

Olorofim demonstrated potent in vitro activity against both *Coccidioides immitis* and *Coccidioides posadasii*. As shown in Table 1, the MICs for olorofim ranged from ≤0.008 to 0.06 µg/ml. The high end of this range corresponded to the low end of that measured for the comparator anti-fungal voriconazole (MIC range, ≤0.03 to 0.5 ng/ml). The geometric mean (GM) MIC of olorofim was also approximately 1.0-fold lower than that of voriconazole, and this difference was significant (0.011 µg/ml versus 0.113 µg/ml; P<0.0001). No differences in the activity of olorolim against *C. immitis* and *C. posadasii* were observed (GM MICs of 0.009 µg/ml against both species). The olorofim and voriconazole MICs against the isolate used to establish CNS infections were 0.015 µg/ml and 0.125 µg/ml, respectively; the fluconazole MIC against this isolate was 16 µg/ml.

TABLE 1

(A, B and C) MICs of olorofim and voriconazole against 59 *Coccidioides* species isolates

1A.

| MIC parameter | All *Coccidioides* isolates (n = 59) | |
|---|---|---|
| (µg/ml) | Olorofim | Voriconazole |
| MIC range | ≤0.008 to 0.06 | ≤0.03 to 0.25 |
| $MIC_{50}$ | ≤0.008 | 0.125 |
| $MIC_{90}$ | 0.015 | 0.25 |
| GM MIC | 0.011 | 0.113 |

1B.

| MIC parameter | *Coccidioides immitis* (n = 21) | |
|---|---|---|
| (µg/ml) | Olorofim | Voriconazole |
| MIC range | ≤0.008 to 0.015 | ≤0.03 to 0.25 |
| $MIC_{50}$ | ≤0.008 | 0.06 |

TABLE 1-continued

| (A, B and C) MICs of olorofim and voriconazole against 59 *Coccidioides* species isolates | | |
|---|---|---|
| $MIC_{90}$ | 0.015 | 0.125 |
| GM MIC | 0.009 | 0.072 |
| 1C. | | |
| MIC parameter | *Coccidioides posadasii* (n = 24) | |
| (μg/ml) | Olorofim | Voriconazole |
| MIC range | ≤0.008 to 0.015 | ≤0.03 to 0.25 |
| $MIC_{50}$ | ≤0.008 | 0.125 |
| $MIC_{90}$ | 0.015 | 0.125 |
| GM MIC | 0.009 | 0.103 |

Marine Model of CNS Coccidioidomycosis—Survival

Figure 3:
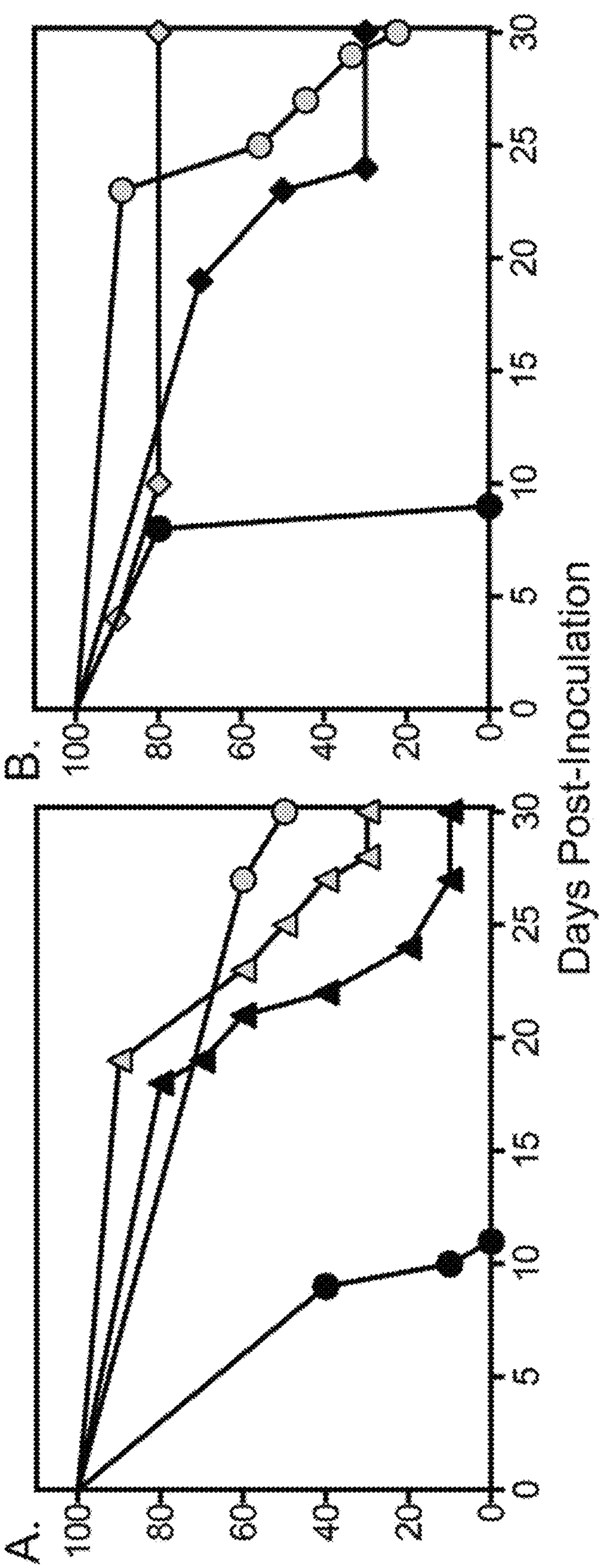
FIG. 3 provides survival curves for mice with CNS coccidioidomycosis treated with olorofim or fluconazole. Black circles, placebo control; grey circles, 25 mg/kg fluconazole administered orally twice daily; black triangles, 10 mg/kg olorofim administered orally twice daily; grey triangles, 20 mg/kg olorofim administered orally twice daily; black diamonds, 6.67 mg/kg olorofim administered orally three times daily; grey diamonds, 13.3 mg/kg olorofim administered orally three times daily.

FIG. 3 provides survival curves for mice with CNS coccidioidomycosis treated with olorofim or fluconazole. Treatment was started 2 days postinoculation and was continued for 14 days. Mice were then monitored without therapy until day 30. (A) First survival study, in which olorofim was administered at total daily doses of 20 and 40 mg/kg, with doses divided into twice daily administrations. (B) Second survival study, in which olorofim was administered at total daily doses of 20 and 40 mg/kg, with doses divided into three times daily administrations. Black circles, placebo control; grey circles, 25 mg/kg fluconazole administered orally twice daily; black triangles, 10 mg/kg olorofim administered orally twice daily; grey triangles, 20 mg/kg olorofim administered orally twice daily; black diamonds, 6.67 mg/kg olorofim administered orally three times daily; grey diamonds, 13.3 mg/kg olorofim administered orally three times daily.

A survival advantage was observed for mice treated with olorofim. For mice administered olorofim twice daily (FIG. 3A), the median survival time was significantly greater than that observed for the vehicle-treated control group (22 and 26 days for the groups treated with 10 mg/kg and 20 mg/kg, respectively, versus 9 days for the control group; P<0.0001 for both comparisons). Similarly, the median survival time was significantly longer for mice treated with fluconazole (30 days; P<0.0001). However, mice dosed twice daily with olorofim began to succumb to infection (day 18) shortly after therapy was stopped (day 15), and the number of mice that survived to the study endpoint was not significantly greater than that in the vehicle-treated control group (10% and 30% versus 0%).

In a subsequent experiment, mice were administered olorofim three times daily. In this experiment, a significant survival advantage was again observed with olorofim (FIG. 3B). The median survival times for both olorofim groups (23.5 and >30 days for the groups treated with 6.67 mg/kg and 13.3 mg/kg, respectively, three times daily) were significantly longer than that for the control group (9 days). The median survival time was also significantly longer for the fluconazole-treated positive-control group (28 days; P<0.0001). The percentage of mice that survived to the study endpoint at day 30 was also significantly greater for mice treated with 13.3 mg/kg olorofim three times daily (80%), compared to control mice (0%; P=0.0007). When the survival results were compared between the two olorofim-treated groups that were administered a total daily dose of 40 mg/kg, either as 20 mg/kg twice daily or as 13.3 mg/kg three times daily, trends toward improvements in the median survival time (26 days versus>30 days; P=0.0643) and the percent surviving (30% versus 80%; P=0.0698) were observed for mice administered more frequent doses.

Fungal Burden and Survival

Figure 4:
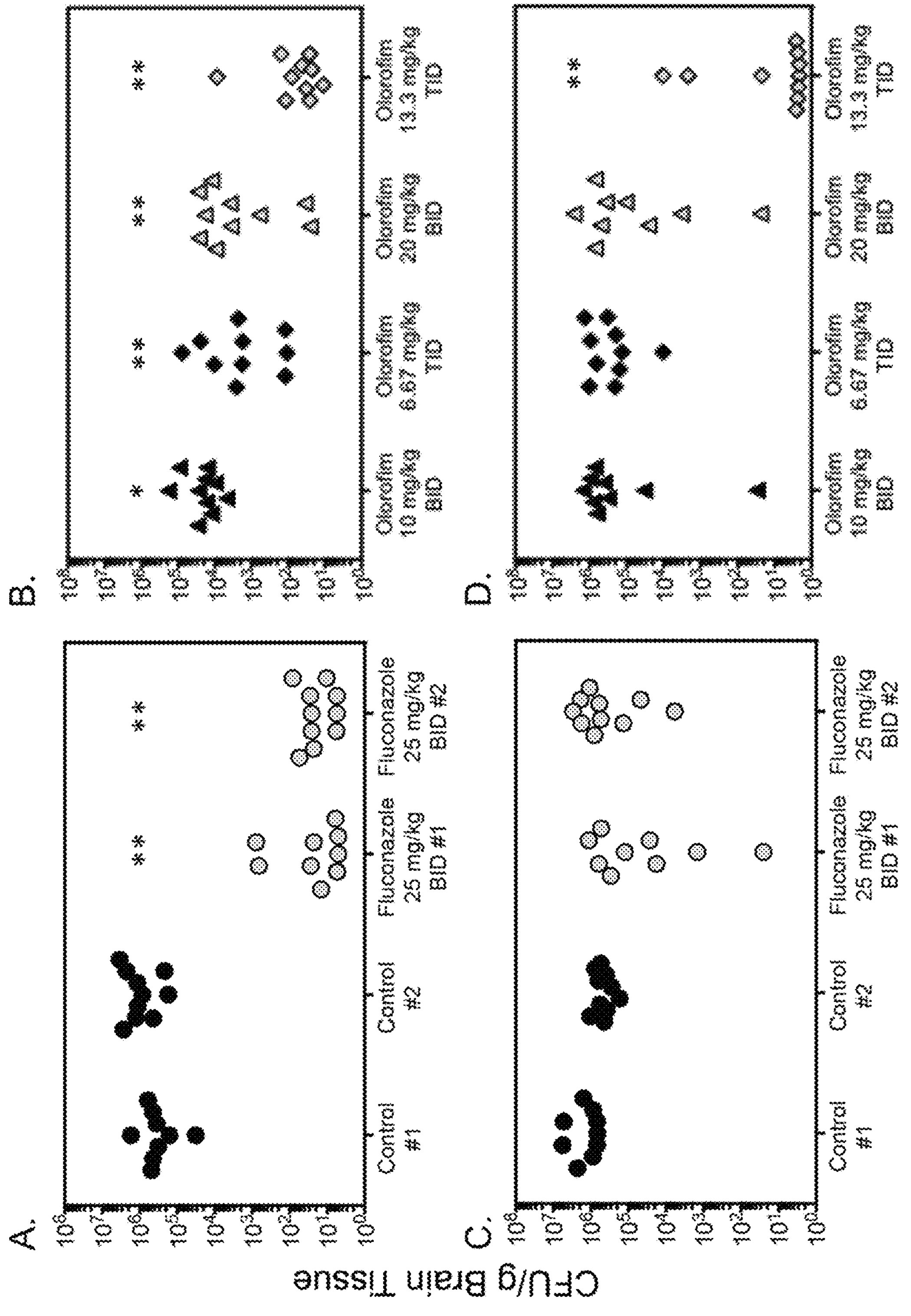
FIG. 4 provides information on brain tissue fungal burdens in mice with CNS coccidioidomycosis secondary to *C. immitis*, in the fungal burden (A and B) and survival (C and D) studies.

FIG. 4 presents results from brain tissue fungal burdens in mice with CNS coccidioidomycosis secondary to *C. immitis*, in the fungal burden (A and B) and survival (C and D) studies. In the fungal burden studies, treatment continued for 7 days, and brains were collected 1 day after treatment was stopped. In the survival studies, treatment continued for 14 days, and CFU were measured at the time of morbidity or at the prespecified study endpoint (day 30). BID, twice daily; TID, three times daily. *, P<0.05; **, P<0.0001.

Treatment with olorofim also resulted in significant reductions in brain fungal burdens. CFU counts for mice treated with olorofim twice daily (mean values of 4.36 and 3.41 log 10 CFU/g for the groups treated with 10 mg/kg and 20 mg/kg, respectively) were significantly lower than those for vehicle-treated control mice (mean value of 5.53 log 10 CFU/g in the experiment in which olorofim was administered twice daily; P≤0.01 for both comparisons) on day 9 postinoculation, 1 day after treatment was stopped (FIGS. 4A and B). Fungal burdens were also significantly lower in mice treated with fluconazole (mean of combined results of 1.33 log 10 CFU/g; P<0.0001 versus control). Similarly, CFU counts for mice treated with olorofim administered three times daily (3.28 and 1.95 log 10 CFU/g for the groups treated with 6.67 mg/kg and 13.3 mg/kg, respectively) were significantly lower than those for vehicle-treated control mice (mean value of 5.97 log 10 CFU/g for the experiment in which olorofim was administered three times daily; P<0.0001 for both comparisons) on day 9 postinoculation in the repeat fungal burden experiment. Consistent with the pharmacokinetic/pharmacodynamic effects observed in a murine model of invasive aspergillosis (Hope W W et al, 2017 supra), increased fractionation of exposure via administration of olorofim three times daily resulted in further reductions in fungal burdens, compared to administration twice daily, and these differences were significant for the groups treated with total daily doses of both 20 mg/kg and 40 mg/kg.

Fungal burdens were also assessed at the time the mice succumbed to infection or on day 30 in the survival experiments (FIGS. 4C and D). For mice administered olorofim twice daily, a rebound in fungal burdens was observed once therapy was stopped; this occurred in both of the olorofim dosing groups, as well as in the group treated with fluconazole. A rebound in fungal burdens was also observed for mice treated with 6.67 mg/kg olorofim three times daily. In contrast, no rebound in fungal burdens was observed for mice treated with olorofim administered at 13.3 mg/kg three times daily, and the CFU counts in that group were significantly lower than those in the vehicle-treated control group (1.13 versus 5.67 log 10 CFU/g, respectively; P<0.0001), Whole-brain homogenates from the group treated with 13.3 mg/kg were also plated, and no fungal colonies were observed for 7 of the 10 mice.

Discussion

In this study, olorofim demonstrated potent in vitro activity against *Coccidioides* species, which also translated into in vivo efficacy in a murine model of CNS coccidioidomycosis caused by *Coccidioides immitis*. The MICs for olorofim were very low (range, ≤0.008 to 0.06 μg/ml). Significant improvements in survival times and reductions in brain fungal burdens also occurred with olorofim treatment.

Interestingly, the in vivo efficacy in this murine model was enhanced with more frequent administration of olorofim. For mice administered the highest total daily dose of olorofim with frequent dosing (40 mg/kg, administered as doses of 13.3 mg/kg three times daily), *Coccidioides* was undetectable within the brains of 7 of 10 mice in the survival arm when the entire brain homogenate was plated. Animals that survived had been drug-free for 14 to 15 days and, given an olorofim half-life of ~2 h in mice, olorofim exposure would have been minimal.

More frequent administration results in higher trough levels, and these results are consistent with a previous study that demonstrated that the minimal concentration ($C_{min}$)/MIC ratio was the olorofim pharmacokinetic/pharmacodynamic parameter most closely associated with efficacy in animal models of invasive aspergillosis (Hope W W et al, 2017 supra). Thus, the in vivo activity of olorofim appears to be independent of the peak concentration. This is consistent with the mechanism of action, which is effectively a starvation mechanism, resulting in the cell being unable to produce DNA and RNA and to undergo protein synthesis when olorofim is present. The administration regimen of three times daily in mice is postulated to keep exposure above trough levels required to maintain pyrimidine starvation and the downstream cellular effects.

Whilst in vivo efficacy was evaluated only against infection caused by one *C. immitis* isolate, it is expected that in vivo activity would be maintained against infections caused by *C. posadasii* or azole-resistant isolates (i.e., fluconazole MICs of ≥64 μg/ml), given the different mechanisms of action of olorofim and the azoles, as well as the results of other studies that demonstrated in vivo efficacy against infections caused by other azole-resistant fungi (Oliver J D et al, 2016. F901318 represents a novel class of antifungal drug that inhibits dihydroorotate dehydrogenase. Proc Natl Acad Sci USA 113:12809-12814; Wiederhold N P et al, 2017. Dihydroorotate dehydrogenase inhibitor F901318 has potent in vitro activity against *Scedasporium* species and *Lomentospora*; and Hope W W et al, 2017 Pharmacodynamics of the orotomides against *Aspergillus fumigatus*: new opportunities for treatment of multi drug-resistant fungal disease. mBio 8:e01157-17).

3. Clinical Activity

Methods: This example describes an open-label single-arm Phase 2b study of olorofim in patients with proven invasive fungal disease (IFD) or probable invasive aspergillosis (IA) AND refractory disease, resistance, or intolerance to available agents. Four patients with coccidioidomycosis (one each with CNS, pulmonary, paravertebral and vertebral, and multisystem disseminated disease) were enrolled. All 4 patients had chronic, well-established infection not responding to therapeutic levels of azole therapy and olorofim was added in each case to the ongoing but incompletely effective background azole therapy.

Results: All 4 patients demonstrated symptomatic improvements within a few weeks of adding olorofim to azole therapy with major reduction or elimination of symptoms. Example case #1: a patient who had disseminated infection (lung, CNS) but primarily with pulmonary complaints had become dependent on supplemental oxygen and use of a walking frame despite therapy with both azoles and amphotericin B over a period of 3 months. Olorofim was added to ongoing posaconazole therapy with the patient noting symptomatic improvement within three weeks. At 3 months, he no longer required the use of oxygen and was able to walk unaided. His Cocci titers also fell from 1:256 on enrolment to 1:8 after 7 months of therapy. Example case #2: a patient with chronic CNS cocci meningitis had ongoing symptoms of chronic headache, nausea, and intermittent vomiting despite 11 years of prior triazole therapy (fluconazole→voriconazole→isavuconazole). The patient noted symptomatic improvement within 4 weeks of adding olorofim to isavuconazole and he continues to be asymptomatic 6 months after initiation of olorofim therapy. The patient remains on combination therapy.

The content of the following patent applications are incorporated herein by reference in their entirety: (1) international application number PCT/GB2015/053546, filing date 20 Nov. 2015 and publication number WO 2016/079536; and (2) international application number PCT/GB2017/051494, filing date 25 May 2017 and publication number WO 2017/203270. All references throughout, such as publications, patents, patent applications and published patent applications, are incorporated herein by reference in their entireties.

The invention claimed is:

1. A method of treating disseminated coccidioidomycosis in a subject, which method comprises:

administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, wherein the disseminated coccidioidomycosis is caused by a *Coccidioides* species selected from the group consisting of *Coccidioides immitis, Coccidioides psoadasii* and a combination thereof.

2. The method according to claim 1, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject twice daily.

3. The method according to claim 1, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject three times daily.

4. The method according to claim 1, which method comprises administering to said subject an effective amount of: 2-(1,5-dimethyl-3-phenyl-1H-pyrrol-2-yl)-N-(4-(4-(5-fluoropyrimidin-2-yl)piperazin-1-yl)phenyl)-2-oxoacetamide.

5. The method according to claim 1, wherein a total daily dose of 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, administered to the subject is from 2 to 50 mg/kg.

6. The method according to claim 1, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered to said subject orally.

7. The method according to claim 1, wherein the subject's fungal burden remains suppressed after cessation of treatment.

8. The method according to claim 7, wherein the fungal burden is the fungal burden in the subject's blood plasma, brain tissue or lung tissue.

9. The method according to claim 7, wherein the fungal burden is suppressed for at least 7 days after cessation of treatment.

10. The method according to claim 1, which method comprises administration to said subject of a pharmaceutical composition comprising an effective amount of 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof, together with one or more pharmaceutically acceptable carriers and/or excipients.

11. The method according to claim 1, which method comprises administration to said subject of a pharmaceutical combination comprising: (i) 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof, and (ii) a second antifungal agent.

12. The method according to claim 11, wherein the second antifungal agent is selected from the group consisting of posaconazole, fluconazole, voriconazole, isavuaconazole, itraconazole and a combination thereof.

13. The method according to claim 11, wherein the second antifungal agent is fluconazole.

* * * * *